US008750693B2

(12) United States Patent
Sharma et al.

(10) Patent No.: US 8,750,693 B2

(45) Date of Patent: Jun. 10, 2014

(54) SYSTEM FOR AND METHOD OF CONSISTENTLY EMITTING A VOLATILE MATERIAL

(75) Inventors: Nitin Sharma, Kenosha, WI (US); Maciej K. Tasz, Racine, WI (US); Ross Peter Jones, Cambridge (GB)

(73) Assignee: S.C. Johnson & Son, Inc., Racine, WI (US)

(*) Notice: Subject to any disclaimer, the term of this patent is extended or adjusted under 35 U.S.C. 154(b) by 380 days.

(21) Appl. No.: 13/196,089

(22) Filed: Aug. 2, 2011

(65) Prior Publication Data

US 2012/0024975 A1 Feb. 2, 2012

Related U.S. Application Data

(60) Provisional application No. 61/369,976, filed on Aug. 2, 2010.

(51) Int. Cl.

| | |
|---|---|
| ***A61L 9/03*** | (2006.01) |
| ***A61L 9/12*** | (2006.01) |
| ***B05B 17/04*** | (2006.01) |

(52) U.S. Cl.

USPC ........... 392/395; 392/403; 422/124; 422/125; 239/44; 239/49

(58) Field of Classification Search

None

See application file for complete search history.

(56) References Cited

U.S. PATENT DOCUMENTS

| | | | | |
|---|---|---|---|---|
| 3,583,642 A | | 6/1971 | Crowell et al. | |
| 3,587,968 A | | 6/1971 | Hennart et al. | |
| 3,828,104 A | | 8/1974 | Barnhurst et al. | |
| 4,323,193 A | * | 4/1982 | Compton et al. | 239/44 |
| 4,413,779 A | * | 11/1983 | Santini | 239/45 |
| 4,419,326 A | * | 12/1983 | Santini | 422/4 |
| 4,913,350 A | * | 4/1990 | Purzycki | 239/44 |
| 5,143,288 A | | 9/1992 | Kohler et al. | |
| 5,143,900 A | | 9/1992 | Steltenkamp et al. | |
| 5,578,563 A | | 11/1996 | Trinh et al. | |
| 5,593,670 A | | 1/1997 | Trinh et al. | |
| 5,891,427 A | | 4/1999 | Mettler | |
| 5,942,217 A | | 8/1999 | Woo et al. | |
| 5,955,093 A | | 9/1999 | Woo et al. | |
| 6,033,679 A | | 3/2000 | Woo et al. | |
| 6,248,135 B1 | | 6/2001 | Trinh et al. | |
| 6,279,834 B1 | | 8/2001 | Fox et al. | |

(Continued)

FOREIGN PATENT DOCUMENTS

| | | |
|---|---|---|
| EP | 0028852 A1 | 5/1981 |
| GB | 1012413 | 12/1965 |
| WO | 9846283 A1 | 10/1998 |
| WO | 2004082726 A1 | 9/2004 |

OTHER PUBLICATIONS

PCT/US2011/046259 International Search Report dated Jan. 16, 2012.

*Primary Examiner* — Joseph M Pelham

(57) ABSTRACT

A system for consistently emitting a volatile material includes a volatile material dispenser having a diffusion element. The system further includes a refill adapted for disposal within the volatile material dispenser and including a container having a volatile material disposed therein and a wick having a first end disposed in contact with the volatile material in the container and a second end extending out of the container. A time constant for (Parameter 4) for the system is less than or equal to about 1.0 hour when estimated using the equation: Predicted mass change=Parameter4+(Parameter3*T)+(Parameter2*exp(−T/Parameter1)).

20 Claims, 25 Drawing Sheets

(56) References Cited

U.S. PATENT DOCUMENTS

| | | | | |
|---|---|---|---|---|
| 6,284,231 | B1 | 9/2001 | Trinh et al. | |
| 6,287,550 | B1 | 9/2001 | Trinh et al. | |
| 6,415,992 | B1 | 7/2002 | Blondeel et al. | |
| 6,592,813 | B1 | 7/2003 | Fox et al. | |
| 7,014,127 | B2 | 3/2006 | Valpey et al. | |
| 7,883,028 | B2 * | 2/2011 | McGee et al. | 239/44 |
| 7,962,017 | B2 * | 6/2011 | Viera | 392/392 |
| 7,997,508 | B2 * | 8/2011 | Motylinski et al. | 239/6 |
| 7,998,403 | B2 | 8/2011 | Uchiyama et al. | |
| 8,043,569 | B2 * | 10/2011 | Tranzeat | 422/124 |
| 8,292,193 | B2 * | 10/2012 | Motylinski et al. | 239/6 |
| 2001/0013352 | A1 | 8/2001 | Poisson et al. | |
| 2002/0032147 | A1 | 3/2002 | Foley et al. | |
| 2003/0150885 | A1 | 8/2003 | Dunne | |
| 2004/0144864 | A1 | 7/2004 | Valpey et al. | |
| 2004/0223871 | A1 | 11/2004 | Woo et al. | |
| 2004/0223943 | A1 | 11/2004 | Woo et al. | |
| 2004/0265196 | A1 | 12/2004 | Varanasi et al. | |
| 2005/0247802 | A1 | 11/2005 | Varanasi et al. | |
| 2006/0097066 | A1 * | 5/2006 | Kvietok et al. | 239/44 |
| 2006/0175425 | A1 * | 8/2006 | McGee et al. | 239/44 |
| 2006/0289669 | A1 * | 12/2006 | McGee et al. | 239/45 |
| 2007/0252017 | A1 * | 11/2007 | McGee et al. | 239/44 |
| 2010/0237162 | A1 * | 9/2010 | Litten-Brown et al. | 239/6 |
| 2011/0284655 | A1 * | 11/2011 | Motylinski et al. | 239/44 |

* cited by examiner

FIG. 9A — Poorly Fractionated: $Pe = \sum_{i=1}^{n} b_i P_i$

FIG. 9B — Mixed Fractionation: $Pe = -\ln(b_{lo})$

FIG. 9C — Well Fractionated: $Pe = \left[\sum_{i=1}^{n} b_i P_i^{-1}\right]^{-1}$

SYSTEM FOR AND METHOD OF CONSISTENTLY EMITTING A VOLATILE MATERIAL

CROSS REFERENCE TO RELATED APPLICATIONS

This application claims the benefit of Jones et al. U.S. Provisional Patent Application Ser. No. 61/369,976, filed on Aug. 2, 2010, and entitled "A Refill for a Volatile Material Dispenser."

REFERENCE REGARDING FEDERALLY SPONSORED RESEARCH OR DEVELOPMENT

Not applicable

SEQUENTIAL LISTING

Not applicable

FIELD OF THE DISCLOSURE

The present disclosure generally relates to refills for volatile material dispensers, and more particularly, to refills having a container with a volatile material disposed therein and a wick in contact with the volatile material.

BACKGROUND OF THE DISCLOSURE

Devices that release vapors into the air are well-known in the art. Generally, the purpose of such devices is to deodorize, disinfect, or add positive fragrance to the ambient air, or to distribute insect repellants or insecticides into the air to kill or repel unwanted pests.

Various types of devices have been employed to dispense vapors into the air. For example, passive dispensing devices are known, wherein a volatile material in a gel, liquid, or solid form is provided within a container. The volatile material is diffused into the surrounding atmosphere and the diffusion may be assisted by the natural airflow within the surroundings. An adjustable vent may be included in such passive dispensing devices to increase and decrease the amount of volatile material emitted from the passive dispensing devices. Aerosol containers have also been employed to eject droplets of volatile material from a pressurized container into a surrounding atmosphere upon activation of a trigger.

Other devices have utilized mechanical or electrical devices to disperse volatile materials into the atmosphere. For example, some devices include a cord and plug extending from the device, a plug extending directly from the device, and/or batteries, to power elements of the device. Such powered devices may include one or more heaters, fans, piezoelectric actuators, or other means, or combination thereof by which the volatile material is dispensed from the device.

One type of powered volatile material emitting dispenser includes a housing and one or more heaters and/or fans disposed within the housing for dispensing a liquid volatile material. The liquid volatile material is disposed within a refill having a container for holding the volatile material and a wick in contact with the liquid volatile material and extending out of the container. The wick is disposed adjacent the heater and/or fan when the refill is inserted into the dispenser. Such powered dispensers may be battery-powered or may include an electrical plug extending therefrom that may be inserted into a conventional electrical socket for powering same.

Volatile materials in the form of fragrances are oftentimes used with dispensers employing heaters. Fragrances generally consist of a number of components, combined in particular proportions to give an intended overall smell or character. Achieving this character during emission of a particular fragrance requires releasing the components at rates and in proportions that match their proportions in the original fragrance. This is much easier said than done. In practice, components of the fragrance have different volatilities where volatility is quantified by a partial pressure of a saturated vapor for each component. The greater the partial pressure, the greater the rate at which molecules are released from a surface of the liquid by evaporation. Dispensers employing evaporation therefore tend to emit the more volatile components in a greater proportion than less volatile components, so that the character of the emitted fragrance at any given point in time is not what was intended (in the original proportions). This evaporation of the more volatile components at a greater rate also changes the overall composition of the fragrance over time, thereby continually changing the composition of the fragrance remaining in the refill (as opposed to the original fragrance composition).

A process called fractionation occurs within the wick wherein, over time, fractionation reduces the concentration of high volatility fragrance components and increases the concentration of low volatility fragrance components at an emanating surface (presumably a tip of a wick and/or outer surface of the wick that is exposed to ambient air) and can lead to the vapor composition matching the original fragrance composition. In many dispensers, this process is too slow to be effective. In other words, fractionation takes many days, but in the first few days of use, an excessive amount of the high volatility components is emitted, thereby resulting in a change in the fragrance composition in the refill before fractionation sets in. Fractionation fails to equilibrate with the changing fragrance composition in the refill, thus resulting in the fragrance and vapor compositions steadily varying over time.

SUMMARY

According to a first aspect of the present invention, a system for consistently emitting a volatile material includes a volatile material dispenser having a diffusion element. The system further includes a refill adapted for disposal within the volatile material dispenser and including a container having a volatile material disposed therein and a wick having a first end disposed in contact with the volatile material in the container and a second end extending out of the container. A time constant for (Parameter 4) for the system is less than or equal to 1.0 hour when estimated using the equation: Predicted mass change=Parameter4+(Parameter3*T)+(Parameter2*exp(−T/Parameter1)).

According to another aspect of the present invention, a system for consistently emitting a volatile material includes a volatile material dispenser having a diffusion element. The system further includes a refill disposed within the volatile material dispenser and including a container having a volatile material disposed therein and a wick having a first end disposed in contact with the volatile material in the container and a second end extending out of the container. A product of an evaporation rate at steady state of the volatile material and a height of a stem of the wick, divided by a cross-sectional area of the wick stem is greater than 6.4e-6 $kg^{-1}$ $s^{-1}$.

According to a further aspect of the present invention, a method of consistently emitting a volatile material includes the step of providing a system for dispensing a volatile material, the system including a volatile material dispenser having a diffusion element. The system further includes a refill adapted for disposal within the volatile material dispenser and including a container having a volatile material disposed therein and a wick having a first end disposed in contact with the volatile material in the container and a second end extending out of the container, the volatile material having an initial composition. The method further includes the step of inserting the refill into the volatile material dispenser and operating the volatile material dispenser such that a time constant for the system is less than or equal to 1.0, thereby causing the system to reach steady state before the initial composition of the volatile material has changed.

BRIEF DESCRIPTION OF THE DRAWINGS

Other aspects and advantages of the present disclosure will become apparent upon consideration of the following detailed description, wherein similar structures have similar reference numbers.

DETAILED DESCRIPTION

The present disclosure is directed to refills for holding volatile materials. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Further, the use of the term fragrance herein does not restrict the present disclosure to solely fragrances. In particular, the principles of the present disclosure apply to any volatile material emitted through a wick by evaporation. Examples of volatile materials include, but are not limited to, for example, a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and combinations thereof. Additives may be included in the volatile material, such as, for example, fragrances, and/or preservatives.

The present disclosure provides a wick-based volatile material dispenser in which fractionation occurs with sufficient speed to emit the volatile material with a consistent vapor composition over time that matches an initial volatile material composition (before any volatile material has been emitted therefrom). The rate of fractionation is measured by a dimensionless quantity, a Peclet number, which is a function of: (1) wick geometry, (2) a volatility of fragrance components of the volatile material, and (3) an air flow that disperses a vapor (of the volatile material) emitted by the dispenser.

Wick Geometry

Figure 1:
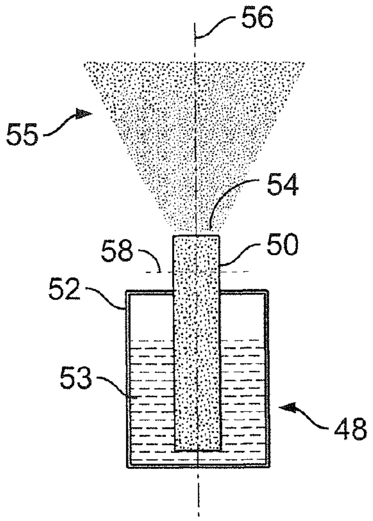
FIG. 1 is a schematic front elevational view of a refill having a wick that is subjected to heat.

A refill 48 of the present disclosure includes a wick 50 that has a generally porous structure that is disposed within a container or bottle 52, as seen in FIG. 1, and in contact with a volatile material 53 therein. The wick 50 extends out of the bottle 52 and terminates in an emanation surface 54 that includes one or more surfaces of the wick 50, wherein volatile material 53 flows through the wick 50 to the emanation surface 54 by capillary action. Vapors 55 of the volatile material are generated at the emanation surface 54 and, as the vapors are released from the emanation surface 54, the volatile material at the emanation surface 54 is replenished by flow from the bottle 52. This flow defines a geometric flow axis 56 for the wick 50 and a wick cross-section 58 is defined as the area that is generally orthogonal to the flow axis 56. The volatile material 53 has an initial refill or bottle composition before any volatile material has been removed from the refill 48. A vapor composition is a composition of the vapor that is emitted from the emanation surface 54. One goal of the present disclosure is to keep the vapor composition as close to the initial bottle composition as possible and to prevent the initial bottle composition from changing over time.

Figure 2A:
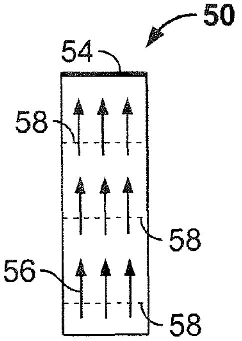
FIG. 2A-2G are cross-sectional views of various embodiments of wicks.
Figure 2B:
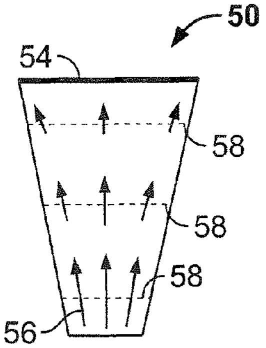
Figure 2C:
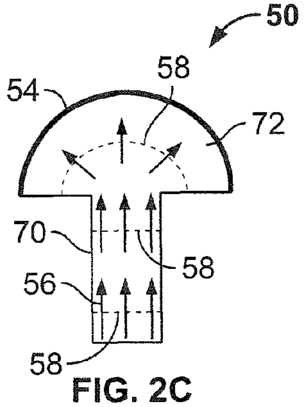
Figure 2D:
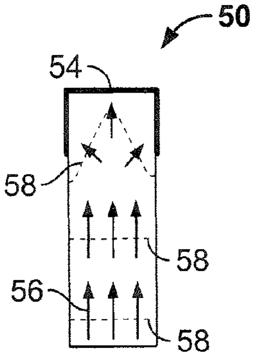
Figure 2E:
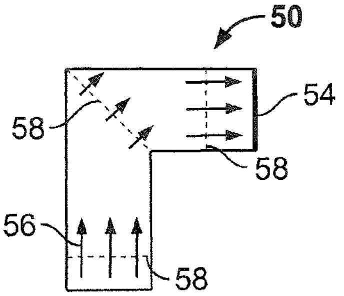
Figure 2F:
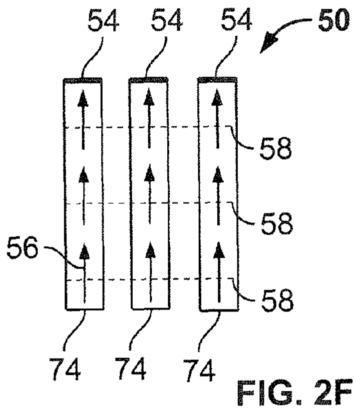
Figure 2G:
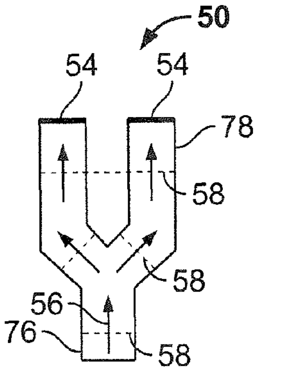
Figure 3A:
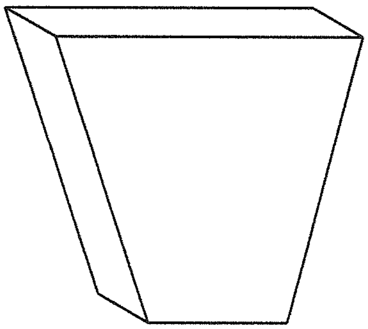
FIG. 3A-3C are isometric views of alternative embodiments of wicks.
Figure 3B:
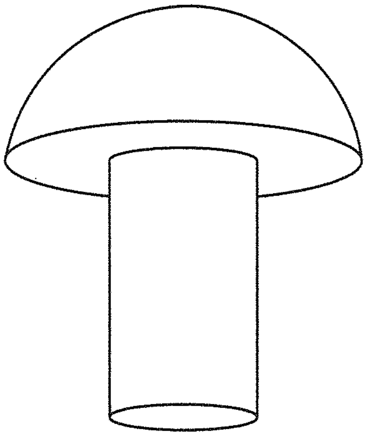
Figure 3C:
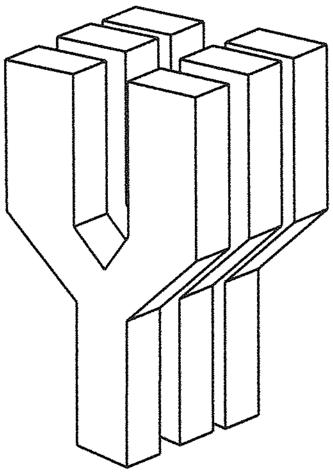

FIGS. 2A-2G depict cross-sections of various wick geometries, wherein such cross-sections are taken along a plane containing the flow axis 56. Each of the wicks 50 includes an emanation surface 54 at an end(s) thereof. The arrows in each wick 50 depict flow velocity vectors, wherein smaller arrows depict a lower speed and larger arrows depict a higher speed. The dashed lines are the cross-sections 58, wherein the cross-sections are orthogonal to the flow axis 56. FIG. 2A depicts a straight wick 50, FIG. 2B shows a tapered wick 50 having a flow velocity that drops as a cross-sectional area of the wick 50 increases, and FIG. 2C illustrates a wick 50 having a straight section 70 and a tapered or mushroomed section 72, wherein an emanation surface 54 and a cross-section 58 of the tapered section 72 are curved. A straight wick 50 having an emanation surface 54 on more than one side thereof is depicted in FIG. 2D, wherein the flow bends into different directions at an uppermost cross-section 58 near the emanation surface 54. Still further, FIG. 2E depicts a bent wick 50 having varying flow velocity vectors and FIG. 2F illustrates the wick 50 with parallel pieces 74, wherein a total cross-section 58 of the wick 50 is taken as the union of the cross-section 58 through each piece 74. Lastly, FIG. 2G shows a wick with a straight section 76 and a branched section 78, wherein the total cross-section 58 of the branched section 78 is taken to be the union of the cross-section across each branch. Other wick designs include a three-dimensional wick geometry, for example, taking any of the cross-sections of FIGS. 2A-2G and extruding it out of the page (see FIG. 3A, wherein FIG. 2B has been lengthened) or rotating it (see FIG. 3B, wherein FIG. 2C has been rotated 180 degrees), or utilizing any two of the sections shown in FIGS. 2A-2G in orthogonal planes (see FIG. 3C, wherein 3 sections of FIG. 2G have been combined).

Physics of Fractionation: Flow Versus Diffusion

Figure 4A:
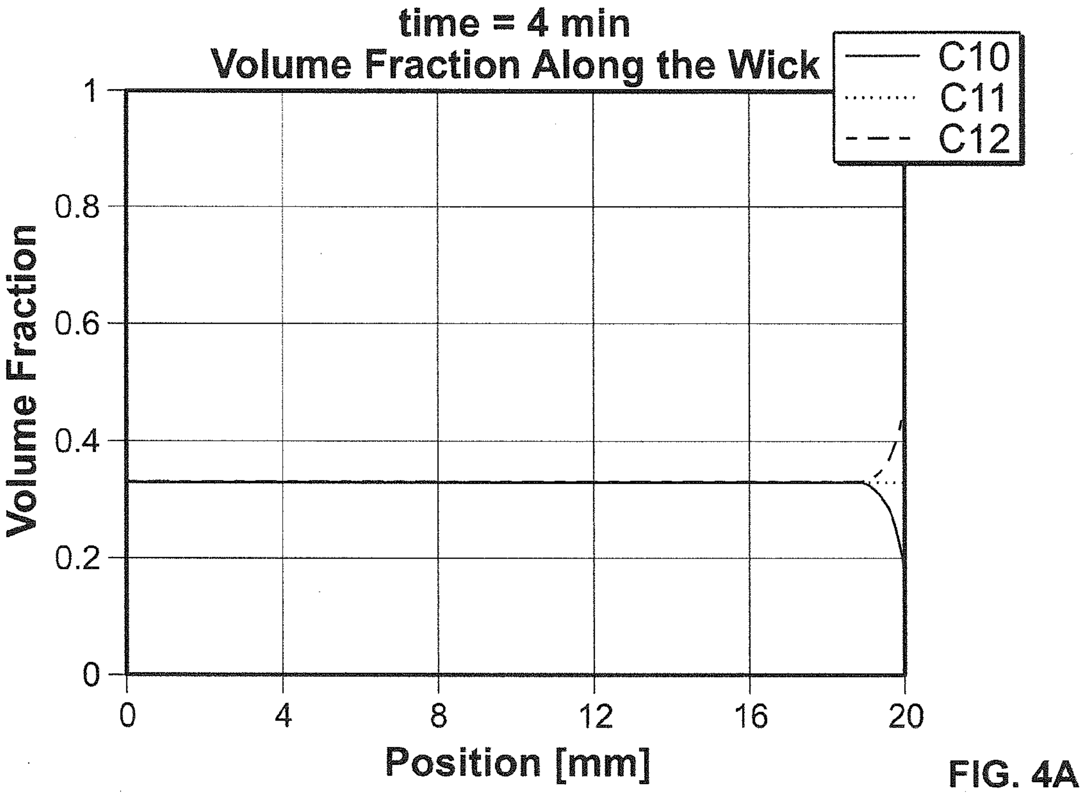
FIGS. 4A and 4B are graphs depicting an evolution of fractionation in a straight wick with a volatile material having three fragrance components.
Figure 4B:
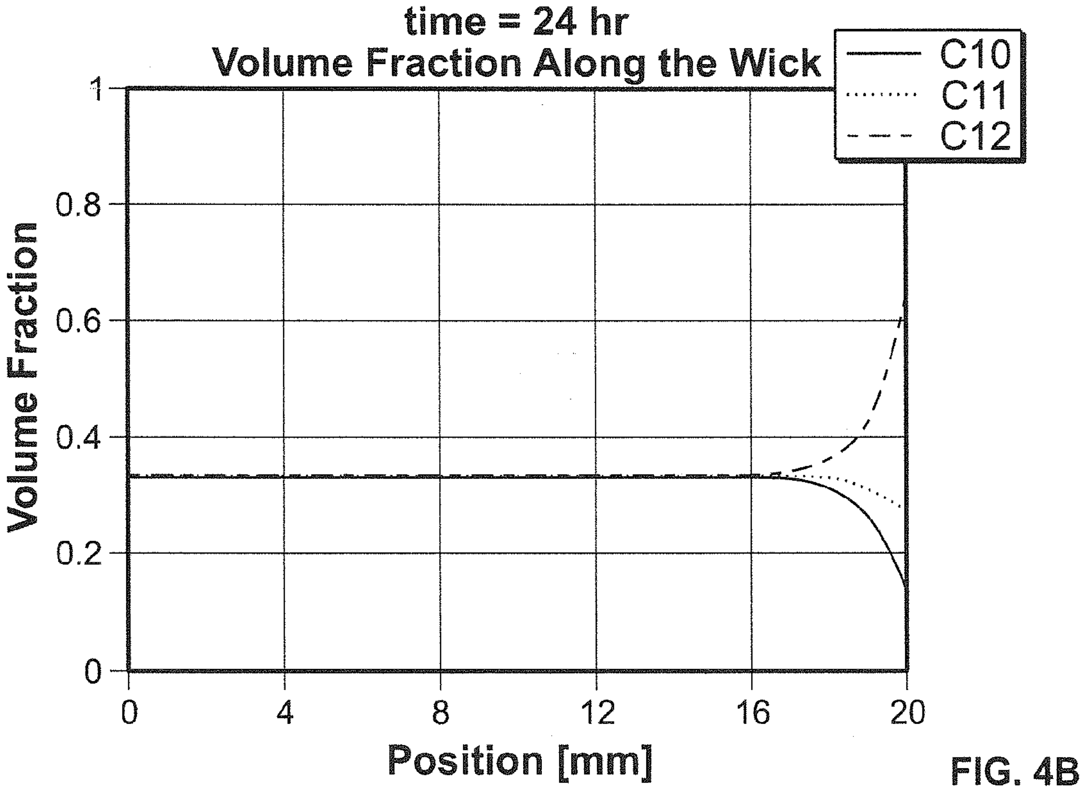

Two processes govern the distribution of fragrance components in the wick: (1) a flow induced by the loss of fragrance at a tip of the wick by evaporation, which occurs in the direction of the flow axis 56 of FIGS. 2A-2G, and (2) mutual diffusion of the fragrance components within the wick, wherein diffusion is a movement of the fragrance components in multiple directions through the wick due to a random, thermal motion of the molecules. Diffusion results in the uniformization of the volatile material composition. Fractionation occurs near the tip of the wick due to a competition between these two processes. FIGS. 4A and 4B illustrate how fractionation occurs and evolves over time. In a first example, a refill includes a bottle having a volatile material with three components therein and a straight wick having a length of 20 millimeters and in contact with the volatile material. At least a tip of the wick is subjected to an air flow that helps in evaporating and diffusing the fragrance components. The components are n-alkanes and are labeled in FIG. 4A by the number of carbon atoms each contains (e.g., the C10 components denotes n-decane). In general, the larger the molecule, the lower its volatility.

The bottle in the example of FIGS. 4A and 4B initially includes a volatile material with three components in equal proportion by volume, and thus the wick initially contains the same three components in equal proportion. When the wick is activated (e.g., by exposing the tip of the wick to air), the C10 component evaporates at a high rate, the C12 components evaporates at a low rate, and the C11 component evaporates at an intermediate rate. The relative volatility of the three components is 6.8:2.6:1, so an initial vapor emitted from the wick is in these proportions, which are far from the original composition of 1:1:1.

FIG. 4A depicts the volume fraction of each component along the length of the wick after a short period of time (about 4 minutes). At the tip (position=20 millimeters), C10 has been depleted and C12 has taken its place (note that the volume fractions must total to 1 at any position along the wick). This decreases the evaporation rate of C10 and increases the evaporation rate of C12, which helps to redress the imbalance in the vapor composition.

Diffusion and flow act together to alter the distribution of the fragrance components. The flow brings fragrance at the bottle composition toward the tip of the wick, which creates concentration gradients within the volatile material along the wick. Diffusion acts in an opposite manner by reducing the gradients. Initially, diffusion has a stronger effect and the distributions spread out. Eventually, a steady state is reached, as seen in FIG. 4B. The nature of the steady state is important for understanding how fractionation can yield a vapor composition that matches the bottle composition (preferably, the initial bottle composition). At any cross-section of the wick, the flux or net flow due to an actual, bulk flow and diffusion of one fragrance component is due to a combination of flow, bringing in new material at the concentration just before the cross-section, and diffusion, where there is a flux that opposes the gradient in concentration. At steady state, a total flux of each fragrance component is fixed, independent of time and position.

In the case of FIG. 4B, there are essentially no composition gradients away from the tip (e.g., below the 16 millimeter position). The component fluxes below 16 millimeters are entirely due to flow and, because the fragrance components are in equal proportion in the bottle, the fluxes are also equal. The fluxes must then also be equal at the tip, which means the vapor composition will match the bottle composition (again, preferably, the initial bottle composition). At the tip of the wick, the concentration of high volatility C10 is depleted, so the flow component of flux is low at the tip, but the flux is enhanced by the diffusion flux. Similarly, the concentration of C12 is enhanced at the tip of the wick, so the flow component of flux is large there but the diffusion flux is in the reverse direction. As another check, the volume fractions of the components at the tip are in inverse proportion to their volatility, which again shows that the fragrance components will be evaporating in equal proportions, so that the vapor composition will match the bottle composition.

Figure 5A:
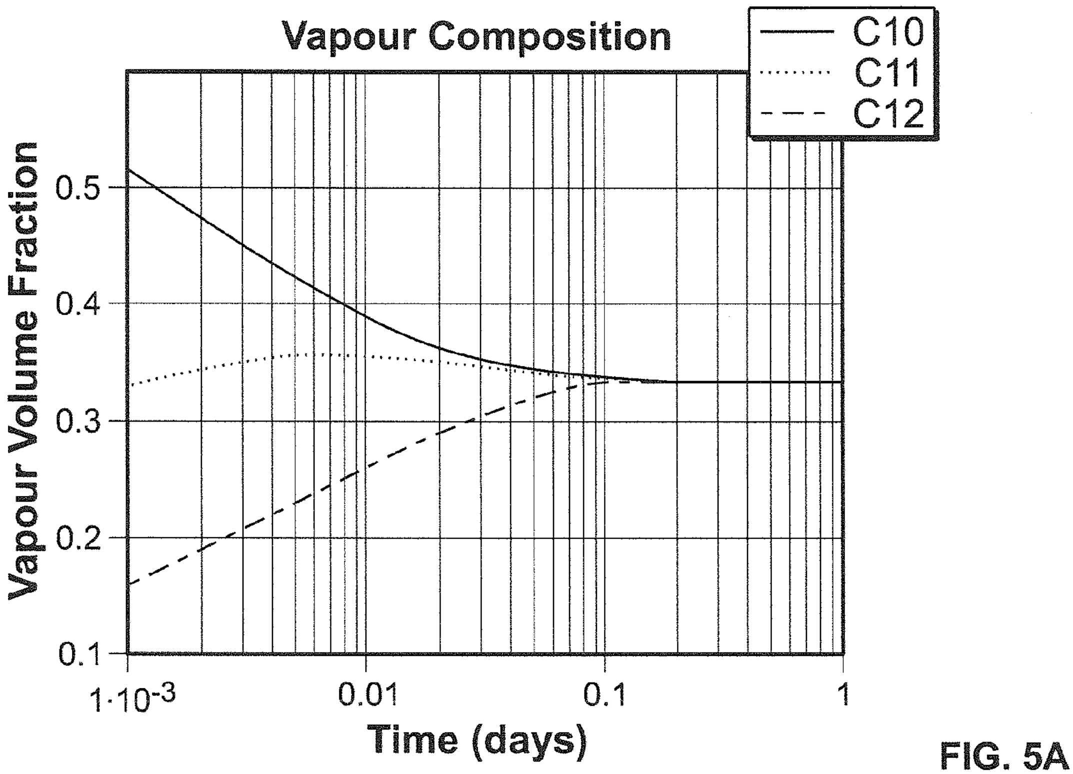
FIGS. 5A and 5B are graphs depicting time evolution for the example of FIGS. 4A and 4B.
Figure 5B:
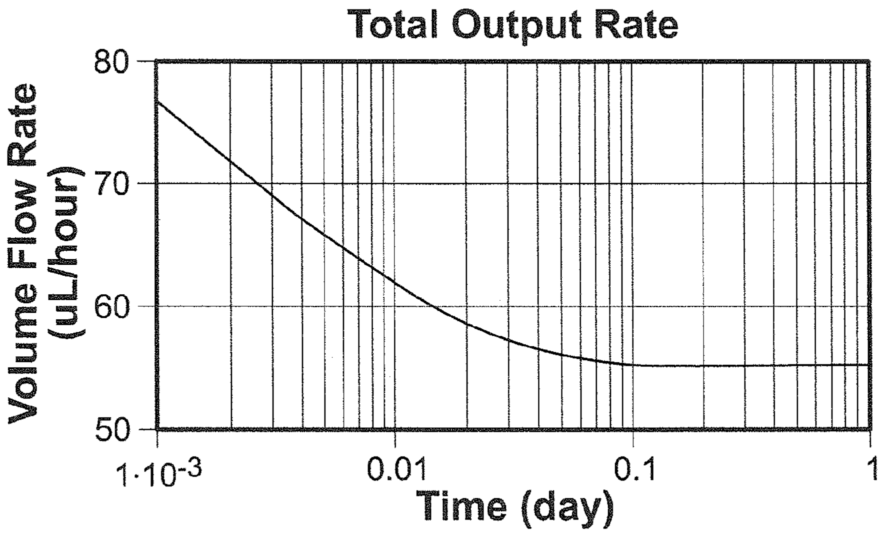

The overall evolution of the system over time is summarized in FIGS. 5A and 5B. FIG. 5A depicts how the vapor composition evolves over time (where time is on a logarithmic scale). The three fragrance components are emitted in equal proportions after roughly 0.1 days or about 2 hours. FIG. 5B shows a total flow or output rate (expressed in mL/hour) of the fragrance composition as a function of time. The total flow rate is initially high due to the vapor initially having a high proportion of the high volatility component, wherein the flow rate drops to its equilibrium value after about 2 hours.

Because the fragrance components of FIGS. 4A-5B are emitted at rates that match the bottle composition, the composition in the bottle does not change with time and the wick continues to deliver a constant vapor composition at a constant rate until the bottle is empty. It is therefore desirous to emit fragrance components as seen in FIGS. 4A-5B.

Figure 6A:
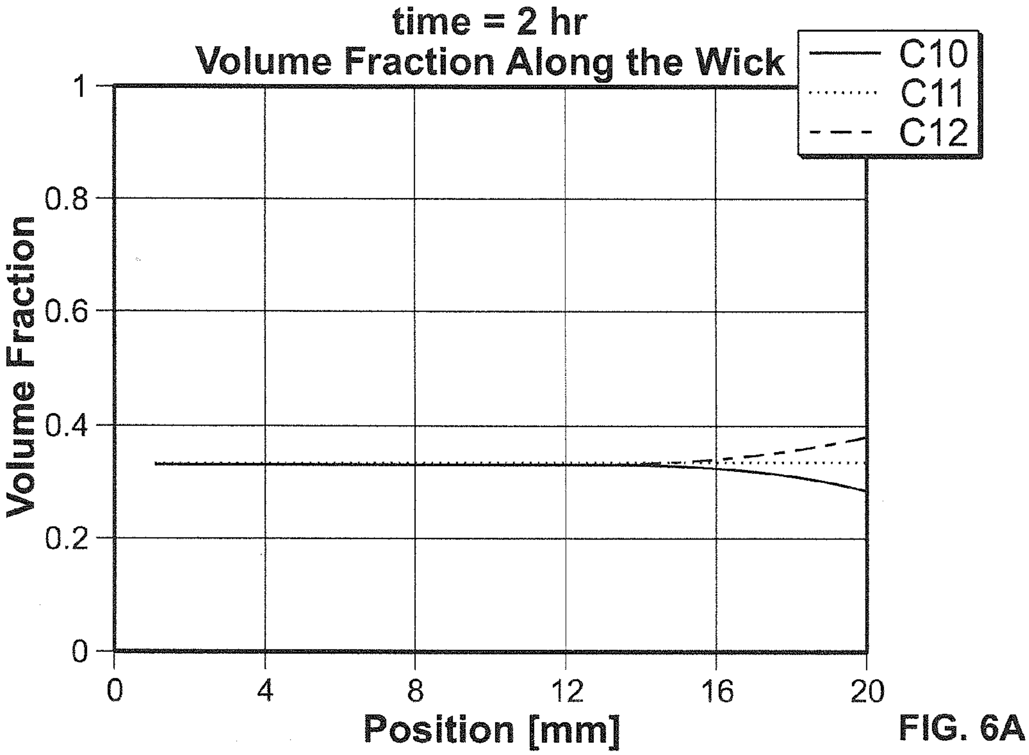
FIGS. 6A and 6B are graphs depicting an evolution of fractionation in a straight wick with a volatile material having three fragrance components.

The example relating to FIGS. 4A-5B is a case where fractionation happens at a sufficient rate to give a stable, consistent vapor output that matches the bottle composition. In a second example, the same wick and fragrance composition is utilized, but the airflow at the tip of the wick is reduced, which then reduces the flow rate. FIG. 6A depicts a distribution of the fragrance components after 2 hours, wherein the higher volatility component, C10, is still depleted at the tip and the lower volatility component, C12, is enhanced in its place. The concentration gradients of the components are not as strong as in FIG. 4A because diffusion within the volatile composition has a stronger effect relative to flow and acts to smooth out the distributions.

Figure 6B:
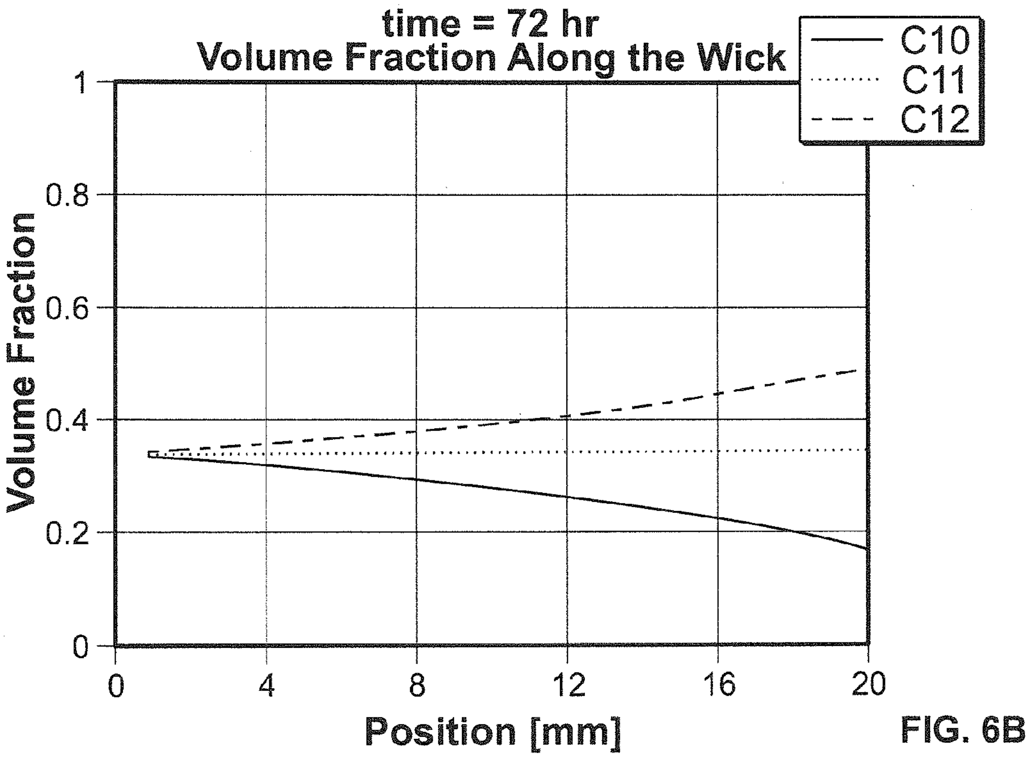

FIG. 6B shows the distribution of fragrance components after 3 days, wherein the distributions have a significant slope between almost the bottom of the wick (position=0 millimeters) and the tip of the wick (position=20 millimeters). Diffusion is therefore affecting the flux of the components along an entire length of the wick. In particular, diffusion affects the flux of fragrance components from the bottle. The flux of C10 is enhanced by diffusion and the flux of C12 is reduced by diffusion, thereby contributing to C10 being released in a greater proportion and C12 in a smaller proportion than the bottle composition.

Figure 7A:
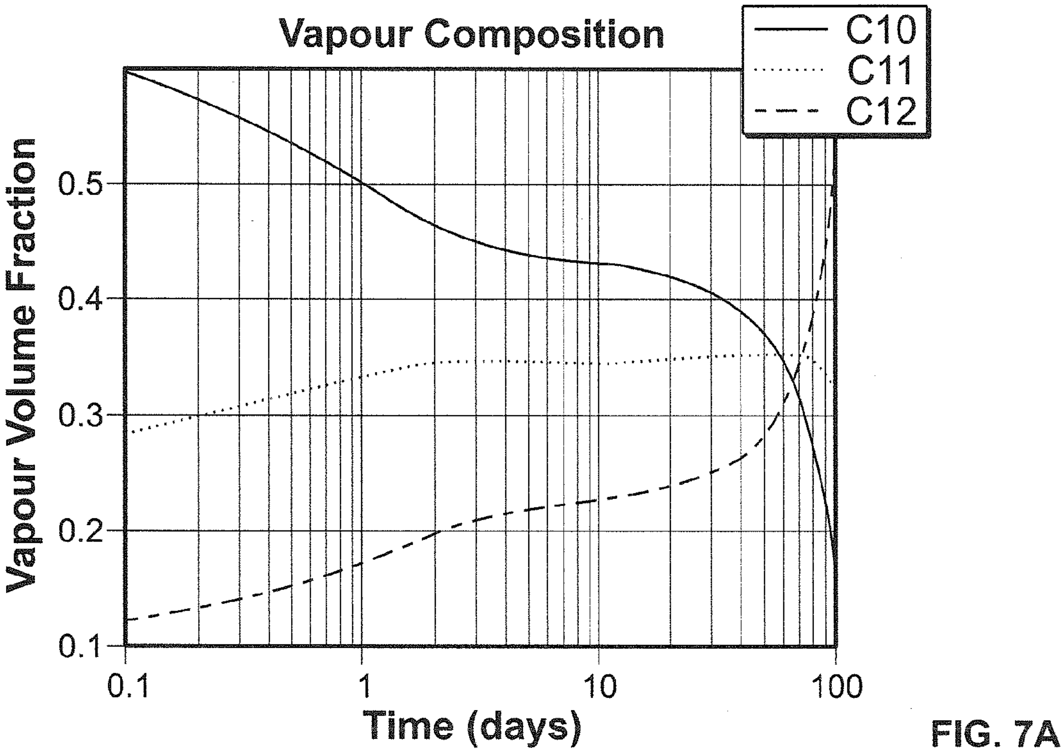
FIGS. 7A and 7B are graphs depicting time evolution for the example of FIGS. 6A and 6B.
Figure 7B:
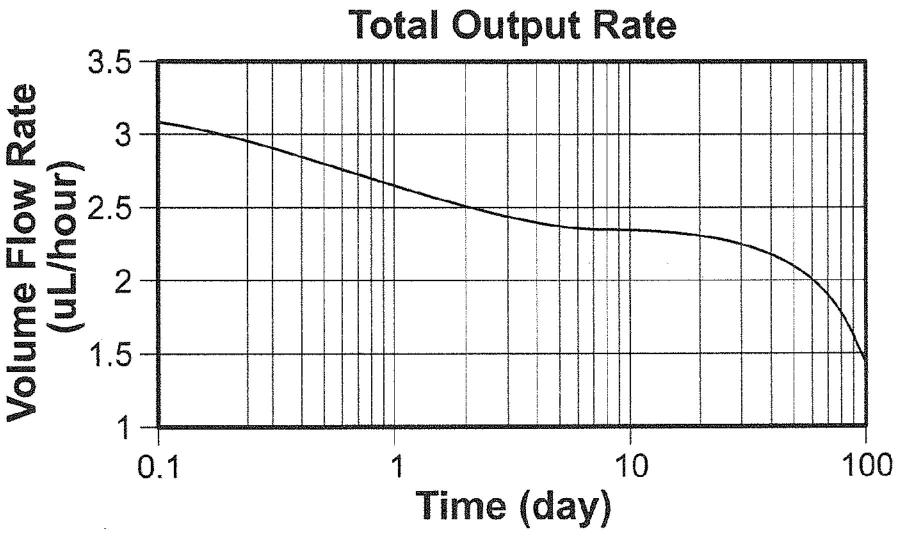
Figure 7C:
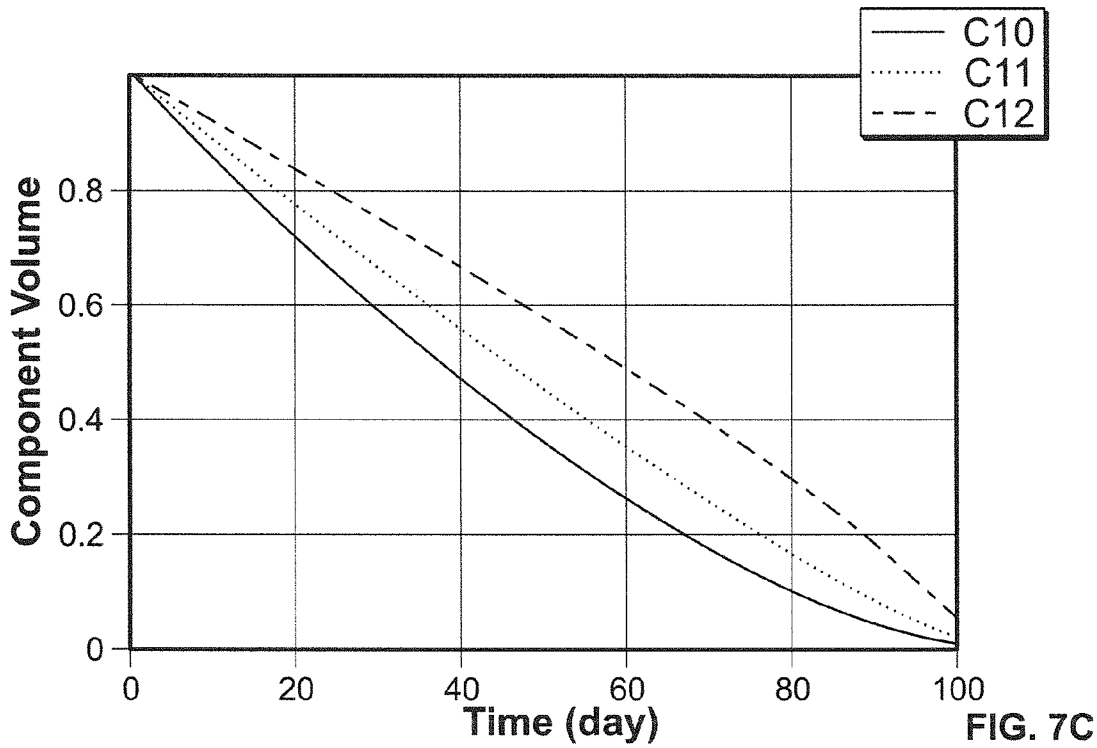
FIG. 7C is a graph depicting a volume of each of the fragrance components of FIGS. 6A and 6B as a function of time and relative to their initial volume.

FIG. 7A shows the vapor composition as a function of time, which tends towards steady state (flattening of all curves) after about 3 days (the total output is almost constant), but continues to drift slowly and never actually reaches equilibrium. This is because the bottle composition is shifting over time, as C10 is being released at a higher rate than C12. FIG. 7C shows the volume of each fragrance component in the bottle as a function of time, relative to its initial volume. For example, after 60 days, the ratio of C10:C11:C12 in the bottle is 0.25:0.35:0.5 (i.e. 1:1.4:2), which is significantly different from the starting ratio of 1:1:1. Eventually, the high volatility components become nearly fully depleted from the bottle while some low volatility components remain, giving a large change in vapor composition. For the same reason, the total output rate drops slowly over time after 3 days, as shown in FIG. 7B. The example of FIGS. 4A-5B (fractionation working well) and the example of FIGS. 6A-7C (fractionation not working well) show that fractionation is effective when the fragrance component distribution gradients are contained within the length of the wick, i.e. they do not extend to the bottle. The flux of the fragrance components in the vapor phase then matches the flux of the fragrance components from the bottle, i.e. in proportions governed by the bottle composition. A comparison of FIGS. 5A and 5B to FIGS. 7A and 7B also shows that well fractionated wicks of FIGS. 5A and 5B equilibrate much more quickly than wicks with poor fractionation, and therefore it is desirous to have a well fractionated wick.

Mathematical Description

Figure 8:
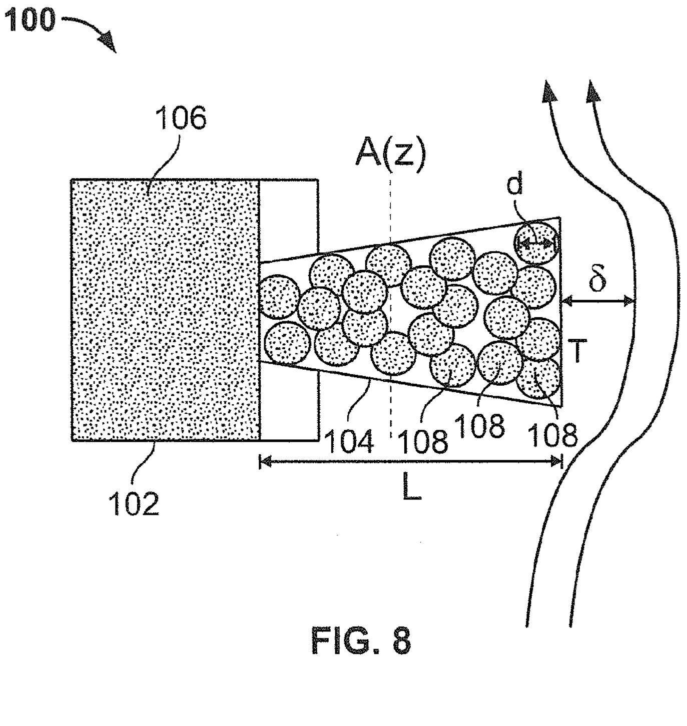
FIG. 8 is a schematic of a volatile material dispenser.

Consider a simple, two-dimensional model of a dispenser, illustrated in FIG. 8. A refill 100 includes a bottle 102 with a tapered wick 104 in contact with a volatile material 106 in the bottle 102 and extending out of the bottle 102. The wick 104 is porous in nature and thus includes pores 108 (i.e., free spaces available for volatile material, wherein the reference numeral 108 points to some, not all, of the pores). The wick 104 further includes an emanating surface 110 from which the volatile material 106 is dispensed. The wick 104 has a length L that extends out of the volatile material 106, with its emanating surface 110 disposed at z=0 and the point where the wick 104 contacts the volatile material 106 in the bottle 102 is disposed at z=−L. A free area of the wick 104 at any point z is A(z), wherein the free area is defined as the cross-sectional area of the wick 104 at point z times the porosity of the wick at point z. A(z) can vary with z either because the cross-sectional area and/or the porosity varies with z.

The bottle 102 contains the volatile material 106 with a mixture of N components, indexed by i=1 . . . N. Assume that a volume fraction of each fragrance component is uniform over the cross-section of the wick 104 at each position z: $f_i \equiv f_i(z,t)$. Note that the volume fractions are subject to the constraint $$\sum_{i=1}^{N} f_i(z, t) = 1.$$

Let Q(t) be the total volumetric flow rate of fragrance at time t. Let D be the mutual diffusivity of the fragrance components. The mutual diffusivity can actually differ between each pair of fragrance components and can also vary with temperature. For "non-ideal" mixtures of fragrances, the mutual diffusivities can also depend on the concentration of the fragrance components. However, in practice, a single number suffices to describe the behavior in the wick: D=2e-9 m2/s is typical for hydrocarbons, for example.

In a porous structure, the value of D needs to be corrected for the tortuosity of the structure, which is the ratio of distance traveled through the pores between two points in the wick to a straight-line distance between those same two points. The tortuosity, in turn, is a function of its porosity (free volume as a fraction of total volume) and topology (e.g., packed spheres, open cell foam, etc.). Formulae for this correction can easily be found in academic literature.

The total volume flux of fragrance component i at position z $\Phi_i(z,t)$, which is the volume of component i passing through the cross-section at z per unit time, is a combination of the flux due to flow and the flux due to diffusion:

$$\Phi_i(z,t) = -A(z)D\partial_z f_i(z,t) + Q(t)f_i(z,t) \qquad \text{EQUATION 1}$$

Summing this equation over i and using the fact that $$\sum_{i=1}^{N} f_i(z, t) = 1$$

shows that Q(t) is the total flux of all the fragrance components at any position along the wick:

$$\sum_{i=1}^{N} \Phi_i(z, t) = Q(t) \quad \text{EQUATION 2}$$

The evolution of the volume fractions comes from conservation of volume (i.e. conservation of mass, taking the liquid fragrance components to be incompressible):

$$A(z)\partial_t f_i(z,t)+\partial_z \Phi_i(z,t)=0 \quad \text{EQUATION 3}$$

The solution to these equations is determined by the initial volume fraction distributions in the wick and boundary conditions at the bottle and the tip of the wick. Let the volume of components i in the bottle be $V_i(t)$. The total volume is $$V(t) = \sum_{i=1}^{N} V_i(t).$$

Assuming the volatile material in the bottle is well mixed, the volume fraction of each fragrance component is $b_i(t)=V_i(t)/V(t)$ and the boundary conditions at the bottle are:

$$f_i(-L,t)=b_i(t)$$

$$\partial_t V_i(t)=-\Phi_i(-L,t) \quad \text{EQUATION 4}$$

The boundary condition at the bottle is that the flux of each component in the liquid phase just inside the tip of the wick has to match the flux of vapor due to evaporation. The following discussion provides a simple model for the evaporation.

Let T be the absolute temperature of the tip of the wick. If the wick only contained fragrance component i, it would produce a vapor at the saturation vapor pressure for that fragrance component, which is a function of temperature, $Psat_i(T)$. For a mixture of fragrance components at the tip of the wick, the partial pressure of the component i just outside the tip of the wick is $f_i(0,t)Psat_i(T)$.

The saturated vapor diffuses away from the tip of the wick and becomes entrained in the air flow around the wick. The effect of the air flow can be described by an equivalent boundary layer thickness δ, which is the thickness of the viscous boundary layer, wherein an edge of a viscous region is found at a point where a velocity of the fluid is essentially equal to the free-stream velocity. Boundary layer thickness is defined such that the flux of vapor from the tip of the wick is the same as that due to diffusion across a layer of still air of thickness δ to a region of zero vapor concentration. In principle, δ can be controlled independently of the wick temperature T. The parameters δ and T, along with the properties of the fragrance components, determine the evaporation flux.

The molar concentration of the vapor for component i just outside the tip of the wick is $f_i(0,t)Psat_i(T)/(RT)$, where R is the universal gas constant, and so the molar flux of component i from the tip of the wick is:

$$F_i(t) = f_i(0, t)\frac{Psat_i(T)}{RT}\frac{Dair_i(T)}{\delta}A(0) \quad \text{EQUATION 5}$$

where $Dair_i(T)$ is the diffusivity of fragrance component i at temperature T. Finally, the volumetric flux of fragrance component i in its liquid phase just inside the tip of the wick is calculated using its molar volume $v_i$:

$$\Phi_i(t)=f_i(0,t)Q_i \quad \text{EQUATION 6}$$

where $$Q_i = v_i\frac{Psat_i(T)}{RT}\frac{Dair_i(T)}{\delta}A(0)$$

The volumetric flow rate $Q_i$ is the flow rate that would be induced in the wick if it only contained component i. Summing Equation 6 over i and using Equation 2 determines the total flow rate:

$$Q(t) = \sum_{i=1}^{N} f_i(0, t)Q_i \quad \text{EQUATION 7}$$

Equations 1, 3, 4, 6, and 7 together give a system of equations that determine the evolution of the component volume fractions in the wick of each component at each point in the wick and at all times and the bottle composition at all times. Most of the results disclosed herein are the result of analyzing these equations, either algebraically or numerically.

Dimensionless System of Equations

Dimensionless equations highlight the key independent factors in a system employing a wick with a volatile material moving therethrough and air flow evaporating the volatile material (such as in FIG. 8). So, scale position z by the wick length, L: x=z/L; x=−L corresponds to the point where the wick contacts the volatile material in the bottle, x=0 corresponds to the tip of the wick; scale area by the tip area: a(x)=A(xL)/A(0); and scale time by the diffusion time for the wick length, $t_D=L^2/D$: $\tau=tD/L^2$. This means that volumes are scaled by A(0)L and volume fluxes are scaled by A(0)D/L. In particular, the total volumetric flow rate becomes a Peclet number, which is a dimensionless form of the total volumetric flow rate, at the tip of the wick:

$$q(\tau) = \frac{Q(\tau t_D)L}{A(0)D} \quad \text{EQUATION 8}$$

Similarly, there is a Peclet number at the tip of the wick describing the volumetric flow rate if fragrance component i completely fills the wick:

$$q_i(t) = \frac{Q_i L}{A(0)D} \quad \text{EQUATION 9}$$

The dimensionless volume flux of component i is:

$$\phi_i(x, \tau) = \frac{\Phi_i(xL, \tau t_D)L}{A(0)D} \quad \text{EQUATION 10}$$

The dimensionless bottle volumes are:

$$\beta_i(\tau) = \frac{V_i(\tau t_D)}{A(0)L},\ \beta(\tau) = \frac{V(\tau t_D)}{A(0)L} = \sum_{i=1}^{N} \beta_i(\tau) \quad \text{EQUATION 11}$$

The system set of equations then become:

EQUATION 12

| | |
|---|---|
| $\phi_i(x,\tau) = -a(x)\partial_x f_i(x,\tau) + q(\tau) f_i(x,\tau)$ | flux equation |
| $a(x)\partial_\tau f_i(x,\tau) + \partial_x \phi_i(x,\tau) = 0$ | evolution equation |
| $f_i(-1,\tau) = b_i(\tau) = \beta_i(\tau)/\beta(\tau)$ | boundary condition at bottle |
| $\partial_\tau \beta_i(\tau) = -\phi_i(-1,\tau)$ | bottle evolution |
| $\phi_i(0,\tau) = q_i f_i(0,\tau)$ | boundary condition at tip |
| $q(\tau) = \sum_{i=1}^{N} q_i f_i(0,\tau)$ | equation for flow rate |

Peclet Number

Analysis of Equation 12 has shown that the behavior of the system depends on the average Peclet number Pe, which is an average of Peclet numbers for the individual fragrance components (as defined below), defined by:

$$Pe = a_{-1} q \text{ and } a_{-1} = \int_{-1}^{0} \frac{1}{a(y)} dy \quad \text{EQUATION 13}$$

The quantity $a_{-1}$ is the harmonic mean of the cross-sectional area of the wick (averaged over its length) relative to the cross-sectional area at the tip of the wick, and will be called the "area factor." The area factor describes all that is important about the shape of the wick. To be explicit:

$$a_{-1} = \frac{1}{L} \int_{-L}^{0} \frac{A(0)}{A(z)} dz \quad \text{EQUATION 14}$$

It is worth emphasizing again that A(z) is the free area at position z, i.e. the geometric cross-sectional area times the porosity. When not stated otherwise, "cross-sectional area" will refer to the free cross-sectional area, which is an area occupied by pores in the cross-section.

For a straight wick or, more generally, for a wick where the cross-sectional area does not vary along a length of the wick, $a_{-1}=1$. For a wick where the cross-sectional area increases from the bottle to the tip of the wick, $a_{-1}>1$. Similarly, an average Peclet number for each fragrance component is defined by:

$$P_i = a_{-1} q_i \quad \text{EQUATION 15}$$

The average Peclet numbers P, for each fragrance only depend on the wick geometry, a temperature at the tip of the wick, and air flow. Pe will vary with time as the total flow rate varies, but if the bottle fractions $b_i$ do not change much with time, then the system will approach equilibrium. The equilibrium value of Pe is the single solution in the range [min($P_i$), max($P_i$)] to the following equation:

$$\sum_{i=1}^{N} \frac{Pe - P_i}{\exp(-Pe)Pe + [1 - \exp(-Pe)]P_i} b_i = 0 \quad \text{EQUATION 16}$$

When not stated otherwise, Pe will refer to this equilibrium, average Peclet number for the entire fragrance composition. The key thing about Pe is that it describes the equilibrium between flow and diffusion in the wick: concentration gradients in the wick are significant over a distance of roughly L/Pe from the tip of the wick. Therefore, the main requirement for good fractionation is that Pe is large.

Other considerations (e.g. response time, as discussed below) show that Pe>4 is especially preferable. For the well fractionated system presented in FIGS. 4A-5B, Pe=23. For the poorly fractionated system presented in FIGS. 6A-7C, Pe=1.

Mathematically it can also be checked that a large Pe gives a vapor composition that matches the bottle composition. At equilibrium, the dimensionless flux of the fragrance component i from the tip of the wick is:

$$\phi_i = \frac{PeP_i}{\exp(-Pe)Pe + [1 - \exp(-Pe)]P_i} b_i \quad \text{EQUATION 17}$$

When Pe is large, so that exp(−Pe) is very small, this just becomes $\phi_i \cong Peb_i$, so the fluxes of the fragrance components are proportional to their bottle fractions, as desired and required.

There is a caveat, however, that when Pe is large, components with very low volatilities can still be under-represented in the vapor composition. Mathematically, "low volatility" means low $P_i$: if Pe is large but $P_i$ is comparable to or less than exp(−Pe)Pe, then $\phi_i \cong Peb_i/[1+\exp(-Pe)Pe/P_i]$, which is less $\phi_i \cong Peb_i$. In practice, this is not a significant issue, for the following reasons: (1) as will be shown hereinafter, in order for Pe to be large, components with low $P_i$ must only be present at very low bottle fractions, $b_i$ (2) the proportion of very low volatility components in the fragrance can be increased to compensate for their lower release rate, (3) the bottle fractions of the low volatility components will slowly increase over time and the compensation can take this into account, and (4) eventually, right near the end of a life of the fragrance in the bottle, all the higher volatility fragrance components are exhausted and only a residue of the low volatility components remains; the user is happy to discard the refill at this point.

Dependence of Pe on Component Peclet Numbers

Figure 9A:
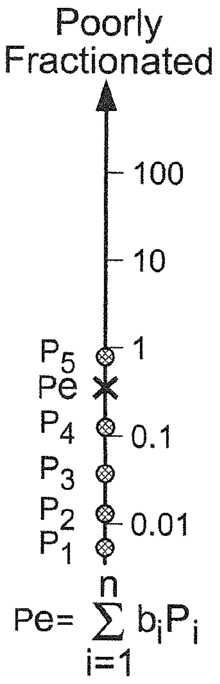
FIGS. 9A-9C depict Peclet number distributions and harmonic means for three fractionation regimes.
Figure 9B:
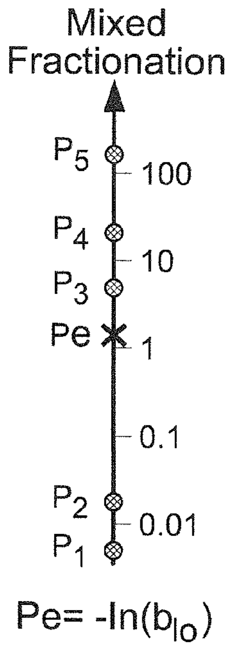
Figure 9C:
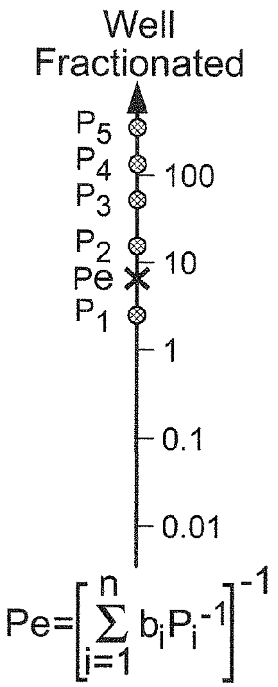

Equation 16 enables the Peclet number Pe to be calculated from the fragrance component Peclet numbers $P_i$ and the component bottle fractions $b_i$. Equation 16 is a complex, non-linear equation. However, analysis of some extreme regimes helps to understand the nature of the solution, wherein three regimes are illustrated in FIGS. 9A-9C. FIG. 9A depicts a "poorly fractionated" regime in which all of the fragrance component Peclet numbers $P_i$ are small and Pe is approximately their arithmetic mean. Pe in FIG. 9A is biased toward the largest $P_i$, but is still small. FIG. 9B depicts a "mixed fractionation" regime in which some fragrance component Peclet numbers $P_i$ are small and some are large. Pe is determined by the combined bottle fraction of all of the low volatility components $b_{lo}$. FIG. 9C depicts a "well fractionated" regime in which all fragrance component Peclet numbers $P_i$ are large and Pe is approximately their harmonic mean, such that Pe is biased toward the smallest $P_i$ but is still large.

FIGS. 9A-9C show that achieving Pe>4 requires all the fragrance component Peclet numbers, $P_i$, to be large (e.g. >1), or for the combined bottle fraction of all the low volatility components to be low, e.g. $b_{lo}$<1.8%.

The following equation (derived from Equations 6, 9, and 15) illustrates how the fragrance component Peclet numbers depend on the fragrance component properties and the design parameters for the dispenser:

$$P_i = V_i \frac{a_{-1}L}{\delta} \text{ where } V_i = \frac{Psat_i(T)Dair_i(T)v_i}{RTD} \quad \text{EQUATION 18}$$

All of the fragrance component properties take effect through a single quantity, the "dimensionless volatility" of the fragrance component, $V_i$, which is only affected by temperature (note that D can also be a function of temperature, although that has not been explicit so far). All of the dispenser geometry (the parameters describing the geometry of the wick and the air flow) takes effect through the term $a_{-1}L/d$, which is the ratio of the "effective length" of the wick, $a_{-1}L$, and the boundary layer thickness of the airflow δ.

Peclet Number and Settling Time

Initially, the wick will contain all fragrance components uniformly at their initial bottle concentrations and will not be fractionated. At first, the high volatility fragrance components will be emitted at a greater rate than low volatility fragrance components. It then takes some time for the wick to approach equilibrium and, if the conditions are right, establish fractionation.

It is very difficult to find analytical solutions for this transient behavior. However, the dimensionless set of equations in Equation 12 shows that the behavior is determined by the area profile, A(x), Peclet numbers of the components at the tip of the wick $q_i$, and their initial bottle fractions $b_i$ (assuming the bottle is large enough that these do not change much during the initial transient), with an overall time scaling factor of $t_D=L^2/D$.

Figure 10:
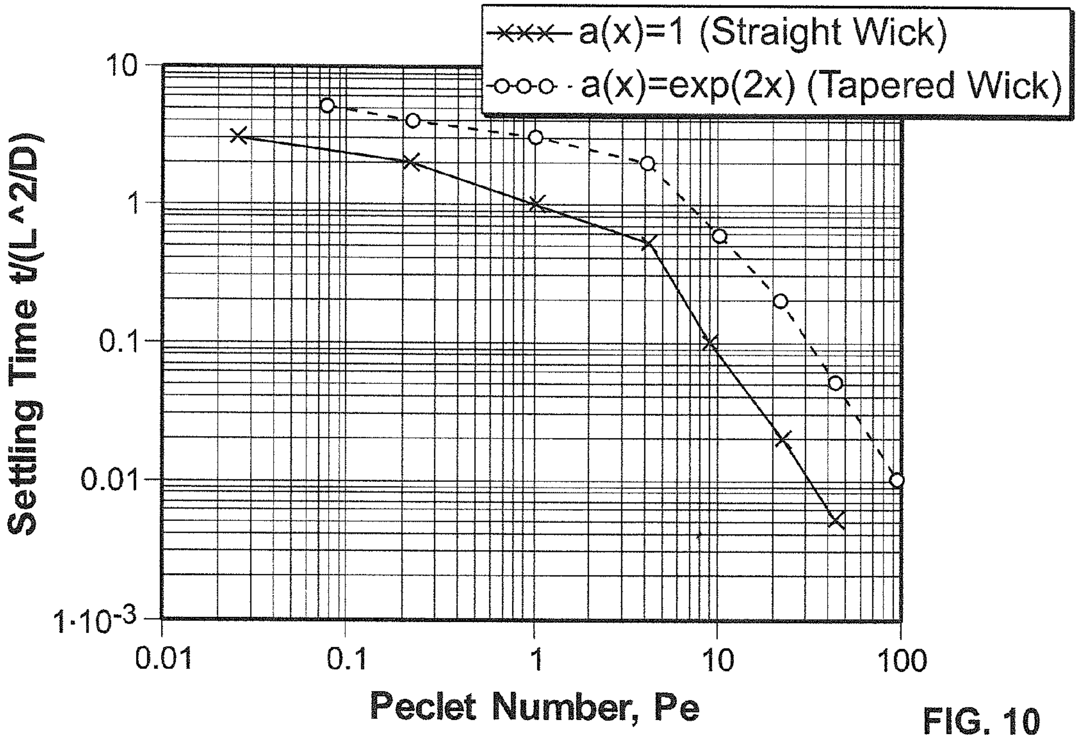
FIG. 10 is a graph depicting a dimensionless settling time versus average Peclet number for a straight wick (solid line) and an exponentially profiled wick (dashed line)

Numerical simulations suggest that a settling time, the time it takes for a wick to approach equilibrium or steady state, primarily depends on the Peclet number Pe and the area factor $a_{-1}$. FIG. 10 shows the dimensionless settling times $\tau_s=t_s/t_D$ versus the Peclet number Pe for a straight wick (solid line with crosses, corresponding to a(x)=1) and an exponentially tapered wick (dashed line with circles, corresponding to a(x)=exp(2x).

For Pe>4, $\tau_s$ is proportional to $Pe^{-2}$. This makes sense because, in a well fractionated wick, the concentration profiles extend over a length L/Pe and the time it takes to diffuse this distance is $(L/Pe)^2/D=t_D/Pe^2$. In addition, $\tau_s$ is larger for the tapered wick. This seems to be accounted for by the area factor $a_{-1}$, which is 1 for the straight wick and 3.2 for the exponentially tapered wick. A power law fit to both curves for Pe>4 is given by:

$$t_s = 10\frac{(La_{-1}/Pe)^2}{D} = 10\frac{(L/qe)^2}{D} \quad \text{EQUATION 19}$$

In other words, although the threshold value for fractionation, 4, is determined by the average Peclet number Pe, the settling time is determined by the average tip Peclet number $qe=Pe/a_{-1}$.

A good way to understand Equation 19 is to rewrite it in terms of the flow speed at the tip of the wick, v(0), instead of its dimensionless equivalent, the tip Peclet number, qe=QL/A(0)D=v(0)L/D:

$$t_s = 10\frac{D}{v(0)^2} \quad \text{EQUATION 20}$$

This, in turn, can be written as:

$$v(0)t_s = \sqrt{10Dt_s} \quad \text{EQUATION 21}$$

The term on the left in Equation 21 is the distance that the fragrance travels due to flow in a period of time $t_s$. The term on the right is essentially the distance that the components would diffuse in that same time. In other words, the settling time is the time interval over which flow and diffusion balance each other out. Over smaller time intervals, diffusion will carry molecules further than flow, but after a time $t_s$, the molecules that have diffused away from the tip of the wick away from the tip and toward the bottle will be brought back by the flow.

For Pe<4, $t_s$ varies like ln(c/Pe) for some coefficient c, although a good fit to the data is difficult to achieve. Nonetheless, the key is that the settling time is large in a poorly fractionated regime. For example, where L=20 mm and D=2e-9 $m^2/s$, $t_D$=2.3 days and in the poorly fractionated regime, the settling time is some multiple of this.

Settling Time for Cycled Output

The required settling time depends partly on user requirements but more specifically on how often the output level of the device is altered. For example, the output level may be altered several times a day, either through manual control by the user or automated control, e.g. by a timer. Consider a dispenser that is alternately turned on for a period of length $t_{ON}$ and off for a period of length $t_{OFF}$, creating a cycle of length $t_{ON}+t_{OFF}$. When the dispenser is turned on, the fragrance component distributions along the wick will evolve toward their equilibrium distributions with a settling time of $t_s=10(La_{-1}/Pe)^2/D$. Assuming Pe>4, the dispenser would reach a well fractionated equilibrium if it was turned on for more than $t_s$. When the dispenser is turned off, the fragrance component distributions will be subject to diffusion only and will relax back to being uniform, with fragrance levels matching the bottle fractions over the diffusion timescale of $t_D=L^2/D$. The long-term behavior of the dispenser depends on how $t_{ON}$ compares to $t_s$ and how $t_{OFF}$ compares to $t_D$.

When $t_{ON}>t_s$ and $t_{OFF}>t_D$, each time the dispenser is turned on is similar to the dispenser being turned on for the first time. During the "on" period, the dispenser reaches its well fractionated equilibrium and during the "off" period it relaxes back to having components uniformly distributed through the wick at their bottle fractions. During an initial period after being turned on, the dispenser will emit the high volatility fragrances at a greater rate than the low volatility fragrances, but this start-up behavior does not significantly affect the average output rates when $t_{ON}>t_s$. So, in this regime, the average vapor composition matches the bottle composition and remains stable from one "on" period to the next.

When $t_{ON}>t_s$ and $t_{OFF}<t_D$, the dispenser does not get time to fully relax during the "off" period. When the dispenser is turned back on, it is already partly fractionated and makes the transition to equilibrium more quickly than when $t_{OFF}>t_D$. This reduces the affect of the initial transient when turned on. As before, the average vapor composition matches the bottle composition quite well and, in addition, the fluctuations in vapor composition are reduced.

When $t_{ON}<t_s$ and $t_{OFF}>t_D$, the dispenser does not have time to reach equilibrium during the "on" period and fully relaxes during the "off" period. The vapor is always released when the dispenser is in a transient state, leading to higher volatility fragrance components being released at a greater average rate than low volatility fragrance components and to the vapor composition varying over time as the higher volatility fragrance components are depleted from the bottle.

When $t_{ON}<t_s$ and $t_{OFF}<t_D$, a new type of equilibrium is possible. When the dispenser is first turned on, the dispenser does not have time to reach static equilibrium. But when the dispenser is turned off, it does not fully relax either, so when the dispenser is turned on the second time, it starts off closer to equilibrium than the first or previous time. After several cycles, the dispenser settles into a periodic pattern, drifting toward static equilibrium during the "on" periods and away from the equilibrium during the "off" periods. The composition of the vapor output of the dispenser may fluctuate during the "on" periods, but provided there is no significant diffusion in or out of the bottle, the average quantity of vapor leaving the tip of the wick matches the average quantity of vapor flowing out of the bottle.

When $t_{ON}$ and $t_{OFF}$ are both small, the dispenser behaves as if it is "pulse width modulated." The fragrance component volatilities are rapidly modulated but the overall behavior of the dispenser is governed by the time average of these volatilities. The fragrance component Peclet numbers $P_i$ can be calculated for these time-averaged volatilities, and the overall Peclet number Pe can be calculated from the fragrance component Peclet numbers $P_i$ just as in the static case. Provided Pe>4, the dispenser will generate consistent output over timescales larger than the cycle time of $t_{ON}+t_{OFF}$, even if the vapor output fluctuates within each cycle.

Figure 11:
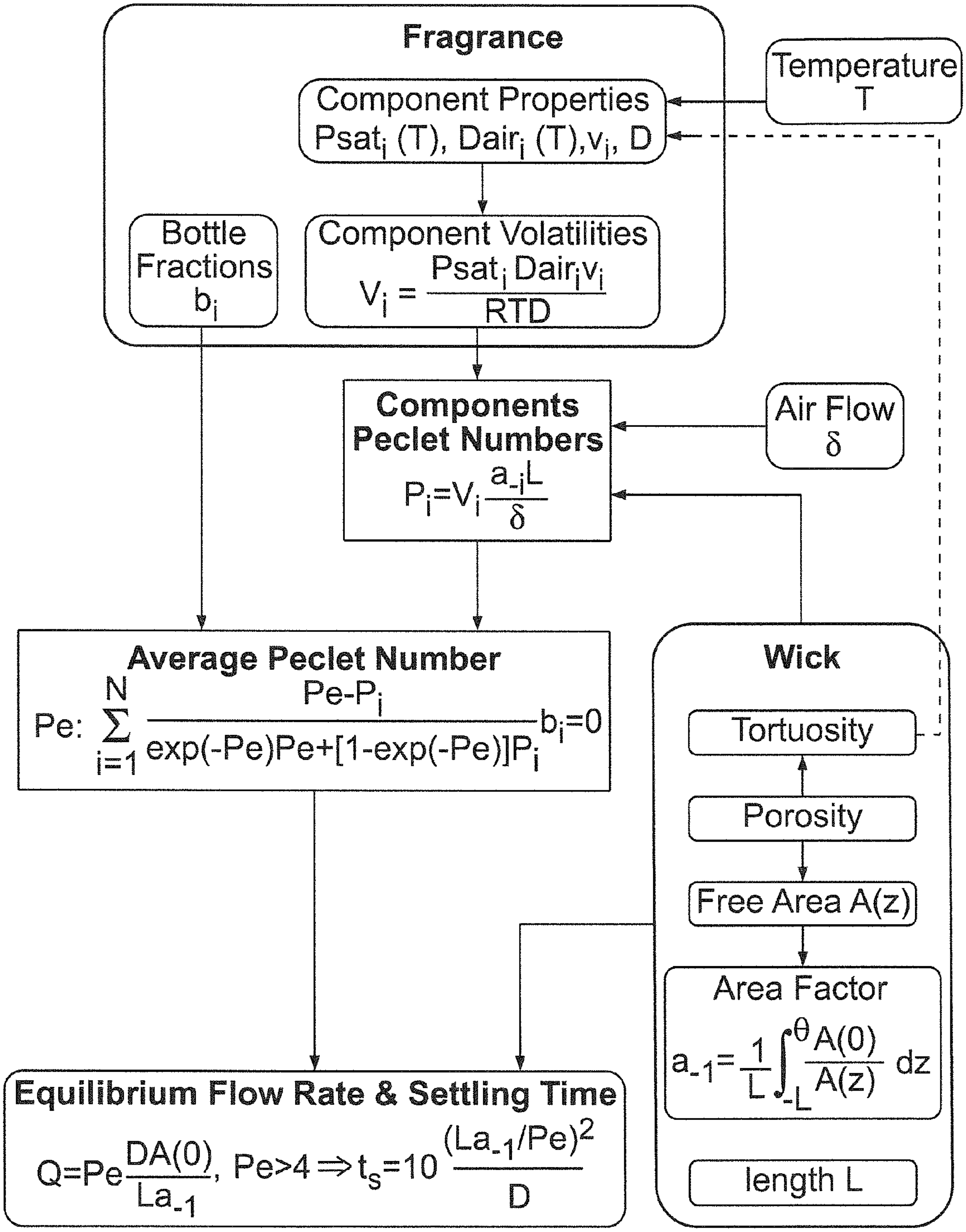
FIG. 11 is a chart summarizing how performance parameters of a volatile material dispenser system depend on design parameters of same.

FIG. 11 depicts the performance parameters of the wick, in particular, the equilibrium flow rate and settling time, which depend on the design parameters relating to the wick, the fragrance, and the air flow. The rectangular boxes contain the dimensionless quantities.

The key design rule for a dispenser that produces a consistent vapor composition and output rate, with a rapid response to changes in output level is Pe>4. The following sections will show how to combine this with other performance considerations to develop design rules.

Surface Tension Dominates—Pore Size Requirement for Porous Wicks

Figure 12:
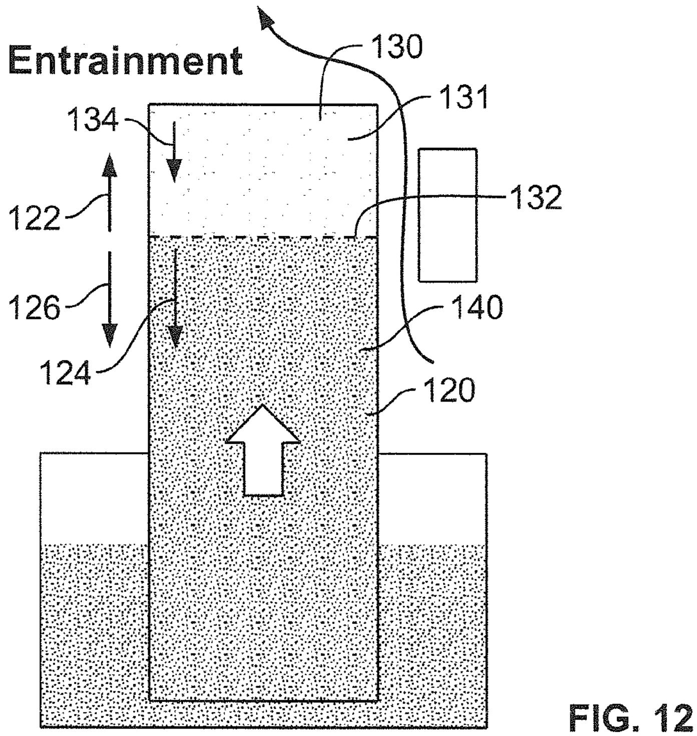
FIG. 12 is a schematic front elevational view of a refill and fluid dynamics therein.

The fluid dynamics within a porous wick can be suitably controlled if the pore size d is chosen suitably. FIG. 12 is a simple schematic of the fluid dynamics in a porous wick 120. The key issue is: what fluid dynamic forces support the flow through the wick 120 to provide the required evaporation rate? Capillary pressure 122, i.e. surface tension, is the primary force drawing the liquid upwards. Capillary pressure 122 is opposed by gravity 124 and flow resistance 126. If gravity 124 and flow resistance 126 are too great, liquid at a top of the wick 120 is not replenished at a rate at which it evaporates, and a top section 130 of the wick dries out at dry section 131. The liquid that evaporates at a wet/dry boundary 132 of the wick 120 produces a vapor that also encounters flow resistance 134 through the dry section 131 of the wick 120, adding to the back pressure on the liquid.

As the wet/dry boundary 132 drops, so does the flow resistance 124 through a wet section 140 of the wick 120 and a gravity head, which is the pressure at a bottom of a column due to a weight of liquid above it The rate of evaporation may also decrease due to the wet/dry boundary 132 reaching a cooler section of the wick 120, lowering the required flow rate. This may enable the wet/dry boundary 132 to reach an equilibrium position at which the capillary pressure 124 is sufficient to maintain the required flow, or the wick 120 may progress to drying out completely.

These fluid dynamics are complicated by the fact that almost every process, such as diffusion, flow resistance due to viscosity, surface tension, etc., that occurs within the wick 120 and the bottle is temperature dependent and some (such as viscosity) are dependent on the mix of fragrance components at any location. The situation is greatly simplified if the capillary pressure dominates, so that the required flow rate can always be maintained, the wet/dry boundary 132 is always held at the top of the wick 120, and any change in flow rate is matched by a slight change of wetted area or the curvature of a meniscus at the top of the wick.

The following calculations support this theory. The wick 120 has a free area A, a pore diameter d, and a length L. The liquid fragrance has a density ρ, a viscosity μ, and a surface tension σ. The bulk flow rate is Q. The maximum capillary pressure is roughly:

$$P_{cap} = \frac{2\sigma}{d} \qquad \text{Equation 22}$$

The gravity head is at most (for a straight, upwards pointing wick):

$$P_g=\rho gL. \qquad \text{Equation 23}$$

The viscous pressure drop is:

$$P_Q = \frac{80\mu Q}{d^2}\int_{-L}^{0}\frac{dz}{A(z)} = \frac{80\mu Q}{d^2}\frac{L}{A(0)}a_{-1}. \qquad \text{Equation 24}$$

where the factor of 80 comes from the Kozeny Carmen model for permeability.

Taking some nominal figures for a typical wick with a typical fragrance: σ=26e-3 N/m, μ=15e-3 Pa·s, ρ=800 kg/m$^3$ for the liquid fragrance; Q=1 mL/day, A=16 mm$^2$, L=50 mm, d=25 um for a straight wick gives $P_{cap}$=2000 Pa, $P_g$=392 Pa, $P_Q$=70 Pa.

As suggested, the capillary pressure dominates. This is somewhat dependent on the pore size. At pore sizes larger than $$d = \frac{2\sigma}{\rho gL} = 133um,$$

the capillary pressure drops below the gravity head. At pore sizes below $$d = \frac{40\mu LQ}{\sigma A} = 0.75um,$$

the flow resistance exceeds the capillary pressure. Nonetheless, this leaves a wide range of pore sizes where capillary pressure can support the flow rate of 1 mL/day without the wick drying out. For example, a pore size of d=10 um easily meets both requirements. In general, the design rule for pore size d is:

$$\frac{40\mu L a_{-1}}{\sigma A(0)} Q << d << \frac{2\sigma}{\rho g L} \quad \text{Equation 25}$$

In particular, a suitable pore size can be found if the term on the left is much less than the term on the right, which places a limit on the flow rate that can be used:

$$Q << \frac{1}{20} \frac{\sigma^2}{\rho g \mu} \frac{A(0)}{L^2 a_{-1}} \quad \text{Equation 26}$$

Putting this in dimensionless terms gives an upper limit on the Peclet number of:

$$Pe = \frac{\dot{m} a_{-1} L}{\rho D A(0)} = \frac{Q a_{-1} L}{D A(0)} << \frac{1}{20} \frac{\sigma^2}{\rho g \mu D} \frac{1}{L}. \quad \text{Equation 27}$$

Note that $\sigma^2/(20\ \rho g \mu D)$ has dimensions of length and encapsulates all the properties of the fragrance. Fortunately, $\delta^2/(20\ \rho g \mu D)$ is usually very large: for the numbers noted above for the typical wick and D=2e-9 $m^2/s$, $\delta^2/(20\ \rho g \mu D)$ equals 144 m. This is much greater than the length of the wick such that Equation 27 does not place any real constraint on Pe. Taking the argument back to Equation 25, this means that there is always a range of pore sizes that can be used. The portion of Equation 27, $$\frac{\dot{m} L}{A}$$

is greater than about 6.4e-6 kg $m^{-1}$ $s^{-1}$, optionally greater than about 8e-6 kg $m^{-1}$ $s^{-1}$, and still optionally greater than about 10e-6 kg $m^{-1}$ $s^{-1}$. In other embodiments, the term $$\frac{\dot{m} L}{A}$$

is less than about 1.e-4 kg $m^{-1}$ $s^{-1}$.

When surface tension dominates, surface tension also prevents the wick from dripping when it is directed downwards. The only caveat to this is that the fragrance needs to be held within individual pores in the wick. If the fragrance can form a continuous film on an outer surface of the wick, the surface tension force is governed by a width of the wick instead of by a diameter of the pores and is usually insufficient to prevent dripping. Dripping can usually be avoided by proper design of the interface between the bottle and the wick, so that fragrance cannot leak from the bottle down the outer surface of the wick.

Surface Tension and Requirements for Capillaries

A capillary is a thin hollow tube. A wick, or a section of the wick, could comprise one or more capillaries in parallel. In the event that the emanating surface is made up of the end(s) of one or more capillaries, the requirement on capillary diameter is essentially the same as that for pore diameter in a porous wick. The only difference is that, in Equation 24 for the viscous pressure drop, the Kozeny Carmen factor of 80 is replaced by the Poiseulle factor of 128/π~41. Given that we are looking for strong inequalities in Equation 25, this is not a significant difference.

Variable Pore Size

A wick may have a pore size that varies along the length of the wick: d=d(z). This could be due to using a porous wick with a graded structure or an assembly of wick sections, e.g. a capillary section feeding a porous section. The equations for capillary pressure and viscous pressure drop then become:

$$P_{cap} = \frac{2\sigma}{d(0)},\ P_Q = 80\mu Q \int_{-L}^{0} \frac{dz}{A(z) d(z)^2} \quad \text{Equation 28}$$

The general requirement that $P_{cap} >> P_Q, P_g$ can still be checked. Given the analysis immediately above, this is still likely to allow a wide range of pore sizes.

Design Method

All of the above findings can be utilized to (1) evaluate a volatile material dispenser to determine if it meets the Peclet number and surface tension criteria discussed above and (2) design a continuously operating or cycled dispenser to meet the performance criteria discussed above.

A design method has been developed to determine the dispenser geometry and operating conditions (e.g., tip temperature and air flow) required to achieve a maximum flow rate for a fragrance. In particular, for any given fragrance, the design method will determine a range of possible geometries and operating conditions. The design method further describes how to select a geometry and operating conditions that suit a number of fragrances. Still further, the design method also addresses how the user will vary the output of the dispenser to provide less than the maximum flow rate, discussed in greater detail hereinafter.

Air flow is parameterized in terms of the boundary layer thickness. In standard dispensers, the boundary layer thickness is a complicated function of the dispenser geometry and the method for generating the air flow. Methods for controlling the boundary layer thickness with simple designs are discussed hereinbelow.

Evaluating a Dispenser Design

Given a wick and a fragrance with a known output rate, the design criteria for good fractionation and dominating surface tension can be checked as follows: (1) determine the wick geometry parameters (length L, tip area A(0), area factor $$a_{-1} = \frac{1}{L} \int_{-L}^{0} \frac{A(0)}{A(z)} dz,$$

and pore size d), (2) determine the bulk fragrance properties (density ρ, surface tension σ, viscosity μ, and diffusivity in the wick D (this includes the effect of wick tortuosity and can be determined, for example, by filling a wick with fragrance and measuring the time it takes for one component to spread along the wick when it is introduced at one end)), (3) determine the output rate Q, and (4) check the Peclet number $$Pe = \frac{Q a_{-1} L}{D A(0)}$$

(good fractionation occurs if Pe>4, a pore size that would allow surface tension to dominate exists if $$Pe << \frac{1}{20}\frac{\sigma^2}{\rho g \mu D}\frac{1}{L},$$

and the actual pore size allows surface tension to dominate if $$\left.\frac{40\mu L a_{-1}}{\sigma A(0)}Q << d << \frac{2\sigma}{\rho g L}\right).$$

Note that these criteria depend on the fragrance properties, so one dispenser may satisfy the criteria with some fragrances and not others.

Designing a Continuously Operating Dispenser

When it comes to designing a dispenser, the design parameters that need to be determined are: (1) the wick geometry (length L, tip area A(0), and area factor $a_{-1}$) and (2) the tip conditions (temperature T and air flow boundary layer thickness δ). There are usually some constraints on these parameters. The geometry of the wick is constrained by the overall envelope or three-dimensional volume the dispenser has to fit within (it can't be too big) and by the manufacturability of the wick (it can't be too small). For each fragrance, there is usually a maximum temperature; exceeding this temperature would cause the fragrance to burn or degrade in some other way. There is also a minimum achievable boundary layer thickness, $\delta_{min}$. For dispensers that operate on forced convection (e.g. fan driven airflow), $\delta_{min}$ is determined by the maximum air speed. For dispensers that operate on free convection, $\delta_{min}$ is determined by the maximum temperature of the heat source that drives the air flow. In both cases, $\delta_{min}$ depends in a complex way on the dispenser geometry, but an order-of-magnitude for $\delta_{min}$ is usually easy to specify.

The dispenser is usually required to work with a range of fragrances. Some of the performance parameters apply to all fragrances, for example: (1) the settling time ts≤tr and (2) the minimum Peclet number Pe 4. Other performance parameters are specific to each fragrance, mainly the maximum output rate, Q. Each fragrance is therefore specified by (1) its properties, such as, the diffusivity in the wick D, the volatility function of each component $V_i(T)$, and the bottle fractions b, (2) the desired performance parameters, such as, the maximum output rate $Q_{max}$, and (3) the constraints on the design, namely, the maximum tip temperature $T_{max}$.

FIG. 11 shows how the performance parameters depend on the fragrance properties and the design parameters in a clearly defined, mathematical way. A range of mathematical methods could be used to find design parameters that satisfy the performance parameters. This section will describe some possible methods that are simple to follow.

Firstly, it is useful to identify the two main trade-offs involved in the design. The first trade-off involves the length of the wick. Increasing the "effective length" of the wick $La_{-1}$, always helps to achieve fractionation, i.e. achieve a high Peclet number, because it helps to remove the component distribution gradients away from the bottle. This can be done by increasing the physical length of the wick L or the amount of taper in the wick, described by the area factor $a_{-1}$, both of which are constrained by the overall size and manufacturability of the dispenser. The length L is also constrained by the need for surface tension to dominate. From Equation 27, achieving Pe>4 while also enabling surface tension to dominate requires:

$$L << \frac{1}{80}\frac{\sigma^2}{\rho g \mu D} \quad \text{Equation 29}$$

This has to be satisfied for each fragrance. However, Equation 29 is not likely to be a practical constraint because the length on the right of the equation is usually on the order of several tens of meters. Therefore, the length and taper should be made as large as the overall envelope for the dispenser allows.

The second trade-off involves the tip area of the wick. If the tip area can be reduced while maintaining the output rate, this increases the flow speed of the fragrance. This helps to achieve fractionation, which is all about the flow overcoming diffusion. It also helps to achieve low settling times, as described by Equation 20. However, increasing the flow speed of the fragrance requires increasing the rate of evaporation from the tip, which in turn requires increasing the tip temperature and/or decreasing the boundary layer thickness. This is limited by the maximum temperature for the fragrance and the minimum achievable boundary layer thickness. As a result, there is a minimum tip area that can be used. As will be shown hereinbelow, designing the dispenser to work with multiple fragrances introduces a trade-off in tip area, which leads to a five-step process for designing a device.

Five-Step Design Methodology

Step 1 in designing a dispenser involves selecting a wick length L and a taper $a_{-1}$ for the wick. A maximum wick length L should be chosen that fits with the allowed envelope for the dispenser or other overall design constraints. Check that the chosen L meets the surface tension criterion for each fragrance given in Equation 2930. A wick taper should also be chosen that achieves the largest possible value of the area factor $a_{-1}$.

Step 2 in designing a dispenser involves calculating a minimum Peclet number $Pe_{min}$. The requirement that the settling time be less than the response time gives a lower limit to the Peclet number as follows:

$$t_s \le t_r \Rightarrow Pe \ge La_{-1}\sqrt{\frac{10}{Dt_r}} \quad \text{Equation 30}$$

$Pe_{min}$ is set to be whichever is larger, the value on the right, or 4, which is the minimum required for fractionation.

Figure 13:
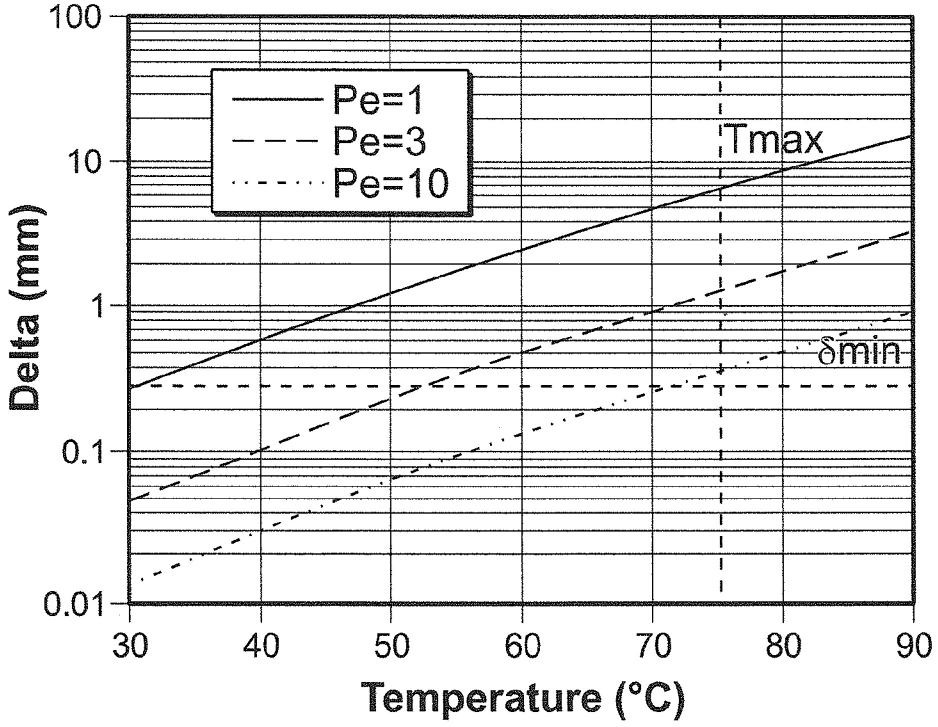
FIG. 13 is a graph depicting a contour plot of Peclet number versus temperature and boundary layer thickness.

Step 3 in designing a dispenser involves calculating a maximum Peclet number $Pe_{max}$ for each fragrance. For each fragrance, Pe can be calculated as a function of temperature T and boundary layer thickness δ. (Equation 18 calculates P, for each component, based on T and δ, and Equation 16 calculates Pe from the component $P_i$'s). Boundary layer thickness versus temperature can be represented as a contour plot; as shown in FIG. 13. As Pe increases, the contours move toward higher values of T and lower values of δ. Imposing the maximum temperature for the fragrance $T_{max}$ and the minimum boundary layer thickness for the dispenser $\delta_{min}$ determines the maximum Peclet number that can be used for that fragrance, $Pe_{max}$. In FIG. 13, $Pe_{max}$ is slightly greater than 10. In some dispensers (e.g., those drive by free convention), the temperature T and the boundary layer thickness δ are related. This can be represented as an "operating line" on the T-6 plot. $Pe_{max}$ is then taken from the point where this line crosses $T=T_{max}$ or $\delta=\delta_{min}$ (taking the first crossing point). If $Pe_{max}$ for a fragrance is less than $Pe_{min}$ calculated in Step 2, then it is not possible to deliver the maximum output rate for that fragrance and achieve fractionation and the desired response time. Checking the calculations in Step 2 will determine if fractionation or response time provides the tighter constraint. Some design trade-off needs to be made: either a lower output rate, or a longer response time, or poor fractionation needs to be accepted (only two out of three can be satisfied). The need to make this trade-off is usually due to the fragrance having an overall low volatility, which usually means there is too large a fraction of low volatility components.

Step 4 in designing a dispenser involves selecting the tip area A(0). There is one equation relating output rate to Peclet number and tip area that applies for all fragrances:

$$Q = Pe\frac{DA(0)}{La_{-1}} \quad \text{Equation 1}$$

Figure 14:
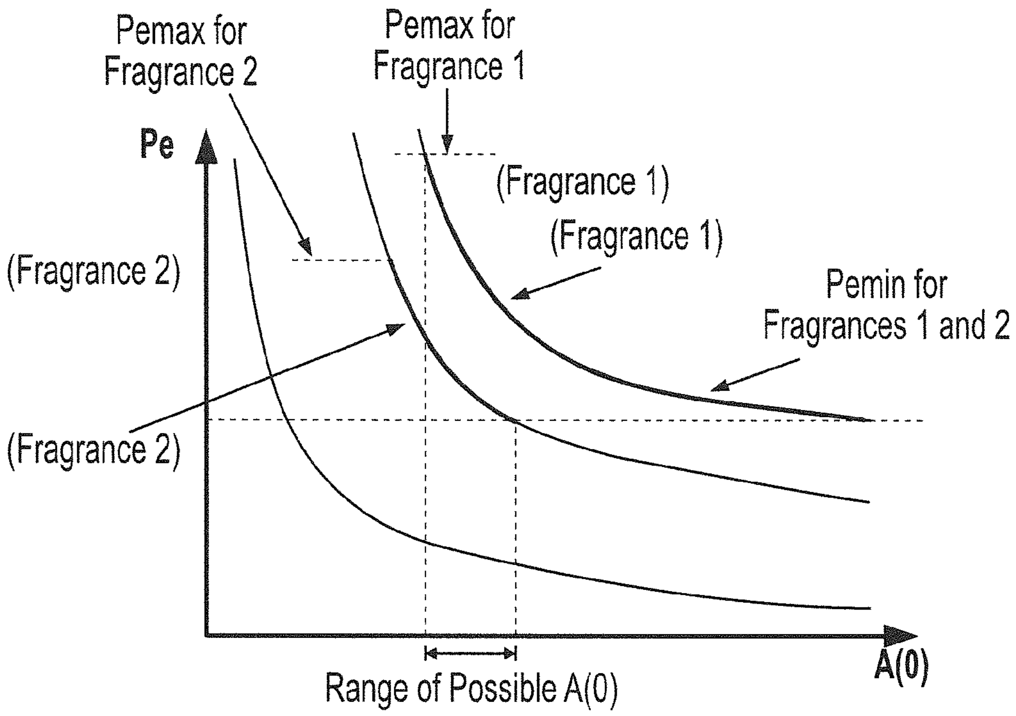
FIG. 14 is a graph depicting a contour plot of output rate versus tip area and Peclet number, showing allowed ranges for each of two fragrances.

Equation 9 can be represented as a contour plot of Q versus A(0) and Pe. The question is whether a tip area A(0) can be chosen so that the maximum output rate $Q_{max}$ for each fragrance can be achieved within the range of Peclet numbers between $Pe_{min}$, calculated for the dispenser in Step 2, and $Pe_{max}$, calculated for the fragrance in Step 3. The requirement for each fragrance can be represented by the segment of the $Q_{max}$ contour that runs between $Pe_{min}$ and $Pe_{max}$. FIG. 14 shows an example of this for two fragrances. The contour segment for each fragrance covers a range of A(0) values. If, as shown in FIG. 14, the ranges of A(0) for all the fragrances overlap, then A(0) should be selected to lie in the overlapping range. If the ranges of A(0) for the fragrances do not overlap, then some compromise is required. If a value of A(0) is selected which lies below the range for some fragrance, it will not be possible to achieve $Q_{max}$ for that fragrance. Achieving $Q_{max}$ would require using excessively high temperatures or an unfeasibly small boundary layer thickness. If a value of A(0) is selected which lies above the range for a fragrance, then $Q_{max}$ for that fragrance can only be achieved with a Peclet number lower than $Pe_{min}$, i.e. by increasing the settling time or losing fractionation (depending on which was the limiting condition in Step 2).

Step 5 in designing a dispenser involves selecting a pore size d. A pore size d should be chosen that satisfies Equation 25 for every fragrance.

Designing a Cycled Device

Hereinabove, it is detailed how a dispenser responds to being cycled on for a time $t_{ON}$ and off for time $t_{OFF}$. There are two regimes where a consistent output is achieved: (1) "Steady on": $t_{ON}>t_s$, so that the device settles down to its steady state behavior in each on period and (2) "PWM": $t_{ON}<<t_s$, $t_{OFF}<<t_D$, and the Peclet number for the time-averaged output rate still satisfied Pe>4.

The design method in the "steady on" regime is identical to that for a continuously operating dispenser. The design method in the "PWM" regime is also identical to that for a continuously operating dispenser, except that the specified output rate should be the average output rate and the component volatilities should also be given their time-averaged values. There is a gray area, where $t_{ON}<t_s$ but $t_{ON}$ is not small enough to fall in the "PWM" regime. One approach to this case is to assume the PWM regime holds (it is the conservative choice because it uses a lower (time-averaged) flow rate) and then check the calculated design by numerically solving the equations in Equation 12 with the PWM modulation applied to the terms $q_i$.

Options for Modulating Output

An important aspect of a volatile material dispenser design is the ability for the user to vary the output. There is a dichotomy in how this is achieved: (1) either the operating conditions—tip temperature and/or air flow—are varied, which results in the Peclet number and settling time varying or (2) the wick geometry is varied, which can be done in a way that preserves the Peclet number and settling time. The equations for Peclet number and settling time can be written in terms of the output rate Q, as follows:

$$Pe = La_{-1}\frac{Q}{A(0)D},\ t_s = \frac{10}{D}\left[\frac{A(0)D}{Q}\right]^2 \quad \text{Equation 32}$$

These equations show that, if the wick geometry (described by $L, a_{-1}, A(0)$) is fixed, reducing the flow rate will reduce the Peclet number and increase the settling time. In particular, reducing the Peclet number risks taking the device into the poor fractionation regime. For example, a first common method for modulating the output rate Q of a dispenser is to vary the tip temperature T and/or the air flow, i.e. the boundary layer thickness δ. This method has the effect of altering the component Peclet numbers, $P_i=V_i(T)La_{-1}/\delta$, and hence the average Peclet number Pe (as determined by Equation 16). In particular, if temperature is decreased or the boundary layer thickness is increased in order to reduce the output rate, this reduces Pe and therefore risks taking the dispenser into the poor fractionation regime.

A second method for modulating the output that does not affect the Peclet number involves varying the tip area A(0). Consider a wick made up of a number of parallel pieces, as shown in FIG. 2F, or a wick made from a parallel bundle of capillaries. The flow can be modulated by varying the number of active pieces or capillaries, e.g. by blocking off the end area of some pieces. The tip area A(0) then relates to the combined area of the active pieces. Each active piece can operate with the same temperature and airflow and has the same length and area factor, and so has the same Peclet number. Note that this method actually varies the cross-sectional area along a whole length of the wick. It is not sufficient to only vary the tip area A(0), for example, by just blocking off part of the tip area in a sintered wick. This just reduces the flow speed below the tip and once the flow speed is unable to compete with diffusion, the wick fails to achieve good fractionation. In terms of the mathematical analysis, herein blocking off part of the tip area would alter the flow field (as illustrated in FIG. 2). This alters the area function A(z), reduces the area factor $a_{-1}$, and hence reduces the Peclet number.

Figure 15:
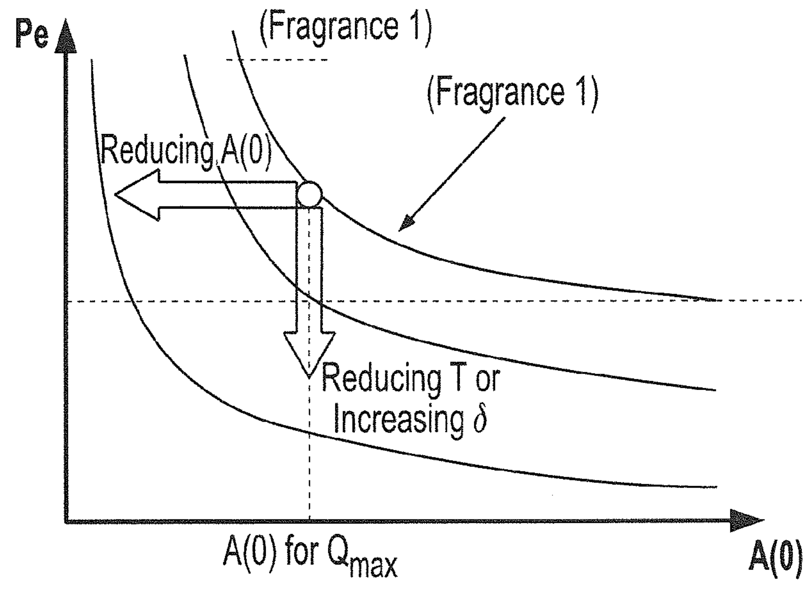
FIG. 15 is a graph depicting a contour plat of output rate versus tip area and Peclet number, showing two methods for varying the output rate.

The choice between the two methods for varying Q (varying the tip temperature T and/or the air flow and varying the tip area) can be illustrated in the Pe-A(0) plot shown in FIG. 15. FIG. 15 shows a black circle where A(0) and Pe are chosen to give the maximum output, $Q_{max}$, for a fragrance; Pe lies within $Pe_{max}$ (determined by $T_{max}$ for the fragrance and $\delta_{min}$ for the dispenser) and $Pe_{min}$ (determined by settling time and fractionation). If the output is reduced by reducing T or increasing d, this corresponds to a vertical path on the plot, crossing the Q contours but also reducing Pe, and so running the risk of going below $Pe_{min}$. If the cross-sectional area is reduced, reducing A(0), this gives a horizontal path on the plot, again crossing the Q contours, but maintaining Pe.

Methods for Controlling Boundary Layer Thickness

Designing a wick involves providing means for controlling the boundary layer thickness of the air flow, 8. In a dispenser utilizing forced convection, i.e. one where the air flow is driven by a pump or fan, δ is determined by the flow rate and the geometry of the dispenser, either of which may be varied. In a dispenser utilizing free convection, i.e. one where the air flow is driven by temperature differences in the system, δ depends on those different temperatures. For example, air flow is driven by air being hot near a heater and cooler above the heater, which creates a chimney-effect. However, in both cases, external factors can have an effect on the air flow and/or temperature, and thus δ. For example, the flow produced by a pump or fan can be affected by objects blocking the air path near an inlet or an outlet of the dispenser. Also for example, the flow produced by free convection can be affected by dispenser orientation, ambient temperature, and/or external heat sources.

Figure 16A:
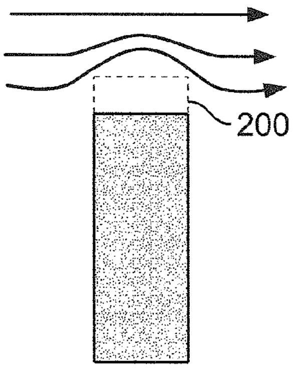
FIGS. 16A-16C are schematic depictions of method for mechanically controlling the boundary layer thickness.
Figure 16B:
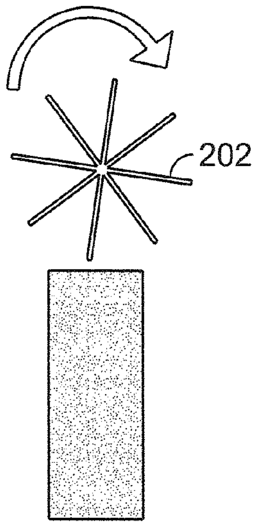
Figure 16C:
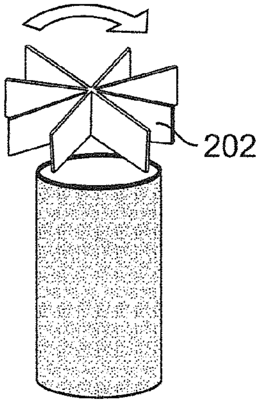

One method for controlling the boundary layer thickness of the air flow δ that is relatively insensitive to external factors is to mechanically define a volume of stagnant air above the emanating surface of the wick, and to pass a fast flow of air over the top of the volume. The total boundary layer thickness is then the sum of the depth of the volume of stagnant air plus the boundary layer thickness of the air flow, but if the air flow is fast enough, the depth of the volume of stagnant air will dominate and will be fixed. The stagnant air volume could be formed by placing a mesh or perforated screen 200 at a fixed distance from the emanating surface, as shown in FIG. 16A. Alternatively, a rotating set of vanes 202 could sweep away the air at some distance above the tip, as shown in FIGS. 16B and 16C. The vanes could be driven by a motor, or by an air flow.

EMBODIMENTS

Application of the Design Methodology Described Hereinabove

The above described design methodology will now be applied to determine wick geometry parameters and operating parameters that satisfy the principles of the present disclosure.

Table 1 below shows the composition of three model fragrances that will be used in the calculations for the embodiments described hereinbelow. The fragrance components are n-alkanes and are identified by the number of carbon atoms in the molecule, n. The "High" fragrance is dominated by small alkanes with high volatility: C8-C12. The "Low" fragrance is dominated by large alkanes with low volatility: C12-C16. The "Mid" fragrance has a broader spread: C8-C16.

TABLE 1

| Reference fragrance compositions, % by mass | | | | | | | | | |
|---|---|---|---|---|---|---|---|---|---|
| #carbons (n) | 8 | 9 | 10 | 11 | 12 | 13 | 14 | 15 | 16 |
| "High" | 20 | 20 | 20 | 20 | 20 | | | | |
| "Mid" | 20 | | 20 | | 20 | | 20 | | 20 |
| "Low" | | | | | 20 | 20 | 20 | 20 | 20 |

Figure 17:
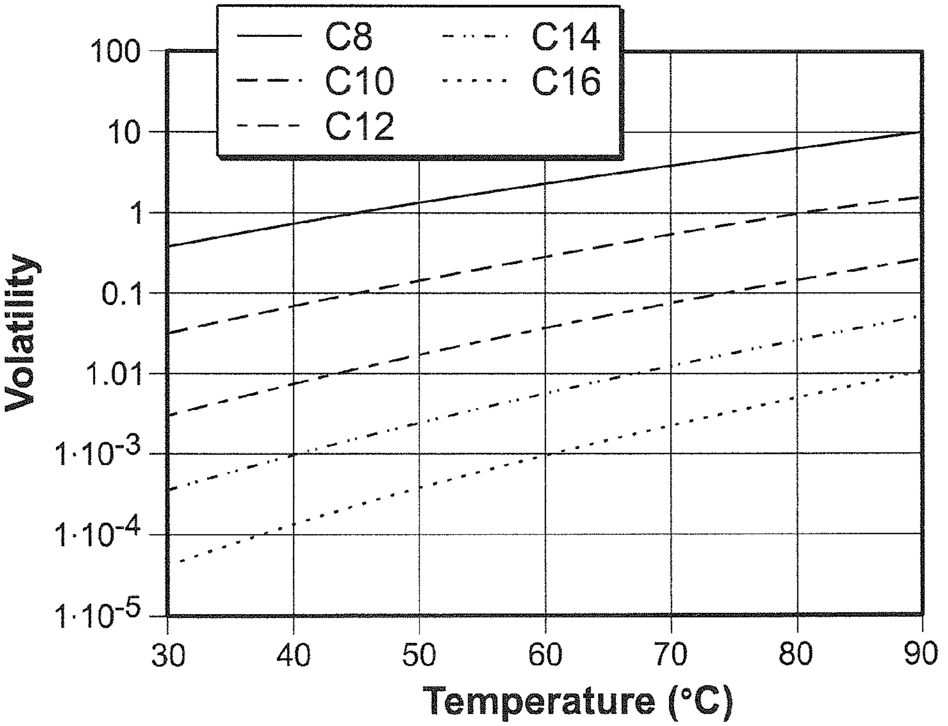
FIG. 17 is a graph depicting volatilities of alkanes with 8, 10, 12, 14, and 16 carbon atoms.

FIG. 17 shows the volatilities of n-alkanes with 8, 10, 12, 14, and 16 carbon atoms as a function of temperature. The volatilities were calculated from Equation 18, using the following data for the alkane properties: saturation vapour pressure data was taken from www.cheric.org/research/kdb/, a liquid density of 800 kg/$m^3$ (for all n) was assumed to calculate molar volumes, a correlation for diffusivity in air was taken from Fuller, Schettler and Giddings, 1966, documented in "Diffusion" by E L Cussler, Third Edition, Section 5.1.3, and a liquid diffusivity of D=2e-9 $m^2$/s was assumed (for all n). The overall fragrance properties and their required output rates are shown in Table 2.

TABLE 2

| Overall fragrance properties | | | | | |
|---|---|---|---|---|---|
| Fragrance | Density (kg/$m^3$) | Viscosity ($10^{-3}$ Pa · s) | Surface tension ($10^{-3}$ N/m) | Maximum temperature (° C.) | Maximum output rate (mL/day) |
| "High" | 800 | 3.5 | 25 | 90 | 1 |
| "Mid" | 800 | 3.5 | 25 | 90 | 0.3 |
| "Low" | 800 | 3.5 | 25 | 90 | 0.1 |

The following design parameters were utilized for the embodiments below: (1) wick length L=50 mm (this is meant to be the longest length that the dispenser design can accommodate; see step 1 above), (2) response time $t_r$=8 hours, (3) porosity of a sintered wick material ∈=0.5, and (4) minimum boundary layer thickness $\delta_{min}$=0.1 mm.

Following Step 1 of the design methodology above, it can be seen that the length easily satisfies the requirement that surface tension dominates:

$$L << \frac{1}{80}\frac{\sigma^2}{\rho g \mu D} = 142 \text{ m},$$

which means that it will be possible to choose a suitable pore size, as discussed hereinbefore.

Embodiment 1

Straight Wick

Consider a straight cylindrical wick of length L and radius r. The tip area of the wick is A(0)=∈π$r^2$ and the area factor is $a_{=1}$=1. The output of the wick will be varied by varying the tip temperature T and/or the air flow via the boundary layer thickness δ. Note that the theories herein concern only the cross-sectional area of the wick, not the shape of that cross-section. For example, the results shown below would also apply to a wick with a rectangular cross-section of width w and depth h, with A(0)=∈wh. Per step 2 above, the minimum Peclet number required to achieve the time response is $$La_{-1}\sqrt{\frac{10}{Dt_r}} = 20.8.$$

This is greater than the value of 4 required for fractionation, so $Pe_{min}$=20.8.

In a forced convection system employing a straight wick, the largest achievable Peclet number occurs at the smallest boundary layer thickness $\delta_{min}$ and the maximum temperature for each fragrance T. Using Equations 16 and 18, the maximum Peclet numbers for the respective fragrances are: (1) "High" fragrance: $Pe_{max}$=402; (2) "Mid" fragrance: $Pe_{max}$=21.5; and (3) "Low" fragrance: $Pe_{max}$=15.1. $Pe_{max}$ for the "Low" fragrance is less than $Pe_{min}$, so it is not possible to achieve both the maximum output rate for that fragrance and the response time and, therefore, some compromise is required.

Figure 18:
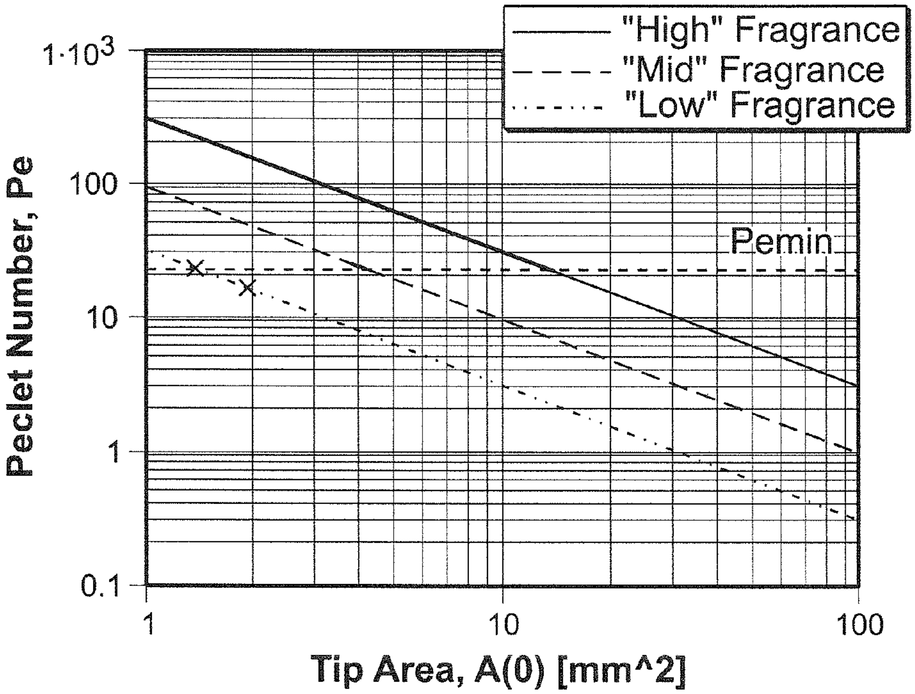
FIG. 18 is a graph depicting tip area versus Peclet number for a straight wick with forced convection.

FIG. 18 shows FIG. 14 applied to the straight wick design. A tip area of A(0)=4 $mm^2$ satisfies the constraints for both the "High" and "Mid" fragrances, i.e. it falls within the thick line segments on their Pe~A(0) curves. For the "Low" fragrance, this choice of A(0) means that the maximum output rate will be achieved at a Peclet number of about 7: fractionation will be achieved, but the settling time will be longer than the desired response time.

Figure 19:
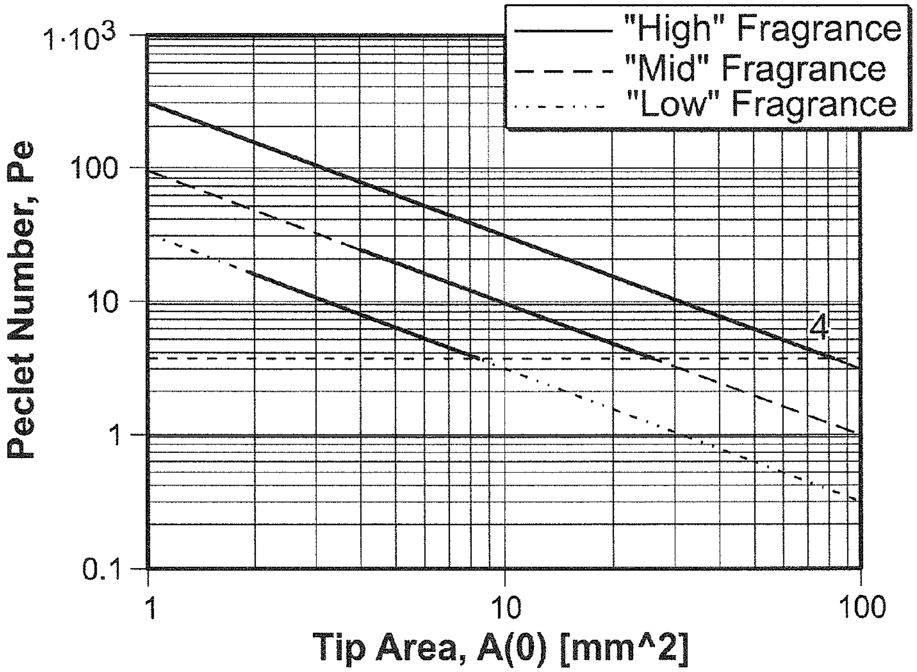
FIG. 19 is a graph depicting tip area versus Peclet number for a straight wick with forced convection, wherein a response time requirement has been abandoned.

FIG. 19 shows the same plot as FIG. 18, but the response time requirement has been abandoned, so that only fractionation determines $Pe_{min}$. A tip area A(0) between 4 $mm^2$ and 7 $mm^2$ would be suitable for all three fragrances. Choosing A(0)=4 $mm^2$, the range of suitable pore sizes is given by Equation 25:

$$0.8\text{ um} = \frac{40\mu La_{-1}}{\sigma A(0)}Q << d << \frac{2\sigma}{\rho g L} = 127\text{ um},$$

where the value on the left is largest for the "High" fragrance. Clearly there is a lot of freedom in the choice of pore size d.

Figure 20:
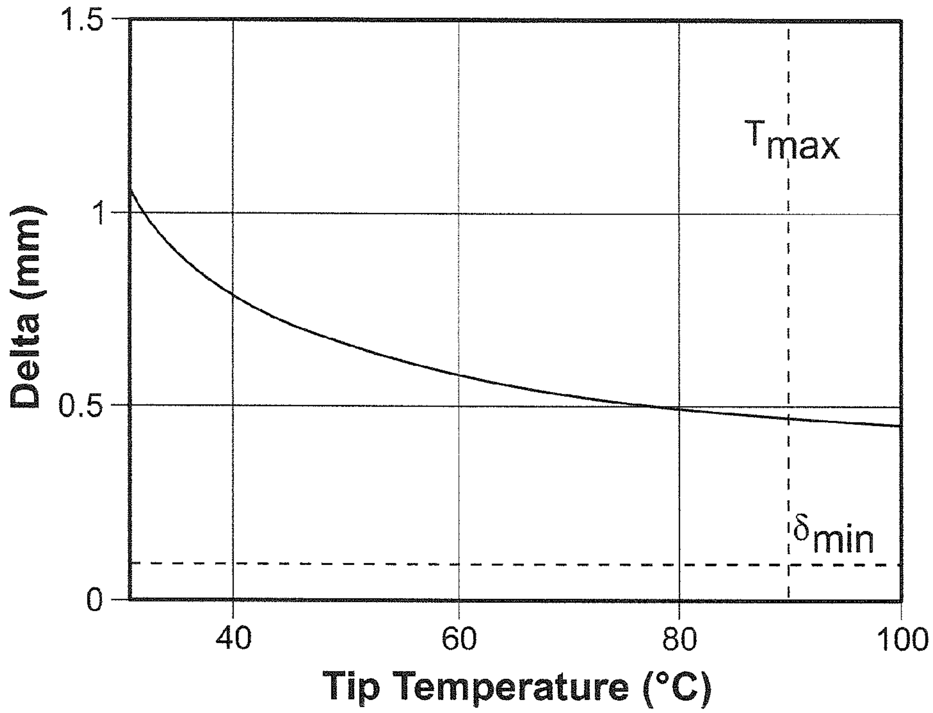
FIG. 20 is a graph depicting temperature versus boundary layer thickness for a device driven by free convention.

In a free convention system employing a straight wick, the tip temperature T determines the air flow and, thus, the boundary layer thickness δ. FIG. 20 shows a plausible δ-T characteristic. The largest achievable Peclet number occurs where the δ-T characteristic first crosses $\delta=\delta_{min}$ or $T=T_{max}$; in this case, $T=T_{max}$ is the limiting condition, where 8=0.46 mm. Using Equations 16 and 18, the maximum Peclet numbers for the respective fragrances are: (1) "High" fragrance: $Pe_{max}$=87.8; (2) "Mid" fragrance: $Pe_{max}$=4.78; and (3) "Low" fragrance: $Pe_{max}$=3.39. $Pe_{max}$ for the "Low" and "Mid" fragrances is less than $Pe_{min}$, so it is not possible to achieve both the maximum output rate for these fragrances and the response time. $Pe_{max}$ for the "Low" fragrance is also less than 4, so it is also not possible to achieve the maximum output rate for this fragrance and fractionation. As with the forced convection case, some compromise is required.

Figure 21:
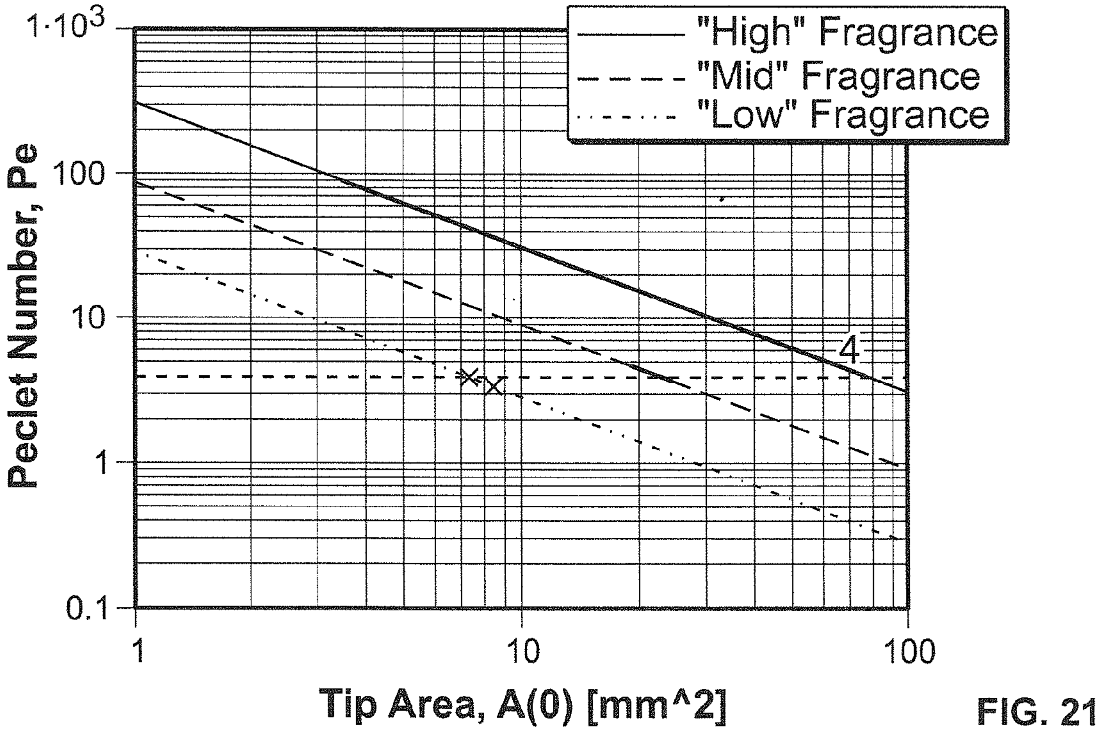
FIG. 21 is a graph depicting tip area versus Peclet number for a straight wick with free convection.

FIG. 21 shows FIG. 14 applied to a free convection system utilizing a straight wick, using only the fractionation requirement for $Pe_{min}$. A tip area of A(0)=20 $mm^2$ satisfies the constraints for both the "High" and "Mid" fragrances, i.e. it falls within the thick line segments on their Pe~A(0) curves. For the "Low" fragrance, this choice of A(0) means that the maximum output rate will be achieved at a Peclet number of about 1.5, which means that fractionation will not be achieved. For the "High" fragrance, this choice of A(0) means that the maximum output rate will be achieved at a Peclet number of 15, less than that required to achieve the desired response time. Choosing A(0)=20 $mm^2$, the range of suitable pore sizes is given by Equation 25:

$$0.16\text{ um} = \frac{40\mu La_{-1}}{\sigma A(0)}Q << d << \frac{2\sigma}{\rho g L} = 127\text{ um},$$

where the value on the left is largest for the "High" fragrance. Again, there is a lot of freedom in the choice of the pore size d.

Embodiment 2

Tapered Wick

Consider a sintered wick of length L that is tapered so that its area factor is $a_{=1}$=4. The output of the wick is varied by varying the tip temperature T and/or the air flow via the boundary layer thickness δ. The minimum Peclet number required to achieve the time response is $$La_{-1}\sqrt{\frac{10}{Dt_r}} = 83.3.$$

This is greater than the value of 4 required for fractionation, so $Pe_{min}$=83.3.

In a forced convention system utilizing a tapered wick, the largest achievable Peclet number occurs at the smallest boundary layer thickness $\delta_{min}$ and the maximum temperature for each fragrance $T_{max}$. Using Equations 16 and 18, the maximum Peclet numbers for each of the respective fragrance are: (1) "High" fragrance: $Pe_{max}$=1610; (2) "Mid" fragrance: $Pe_{max}$=86.0; and (3) "Low" fragrance: $Pe_{max}$=60.2. $Pe_{max}$ for the "Low" fragrance is less than $Pe_{min}$, so it is not possible to achieve both the maximum output rate for that fragrance and the response time, thus, some compromise will be required.

Figure 22:
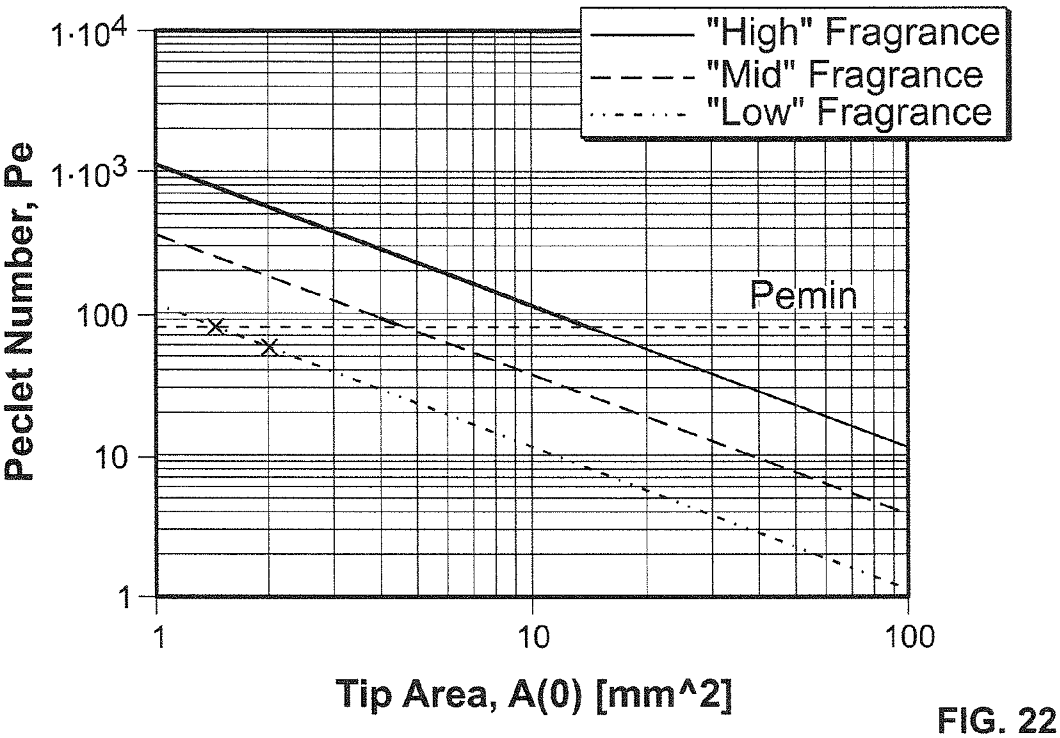
FIG. 22 is a graph depicting tip area versus Peclet number for a tapered wick with forced convection.

FIG. 22 shows FIG. 14 applied to the tapered wick design. A tip area of A(0)=4 $mm^2$ satisfies the constraints for both the "High" and "Mid" fragrances, i.e. it falls within the thick line segments on their Pe~A(0) curves. For the "Low" fragrance, this choice of A(0) means that the maximum output rate will be achieved at a Peclet number of 30 and, therefore, fractionation will be achieved, but the settling time will be longer than the desired response time.

Comparing FIGS. 18 and 22 shows that the taper in the wick has increased all of the Peclet numbers, making fractionation easier to achieve, but the response time requirement is still limiting and a compromise is still required. Choosing A(0)=4 $mm^2$, the range of suitable pore sizes is given by Equation 25:

$$0.8\text{ um} = \frac{40\mu La_{-1}}{\sigma A(0)}Q << d << \frac{2\sigma}{\rho g L} = 127\text{ um},$$

where the value on the left is largest for the "High" fragrance. Again, there is a lot of freedom in the choice of pore size d.

In a free convention system employing a tapered wick, we will assume that the same δ-T characteristic as shown in FIG. 20 and as used for the straight wick applies. Again, the largest achievable Peclet number occurs at $T=T_{max}$ and 6=0.46 mm. Using Equations 16 and 18, the maximum Peclet numbers for the respective fragrances are: (1) "High" fragrance: $Pe_{max}$=350; (2) "Mid" fragrance: $Pe_{max}$=18.8; and (3) "Low" fragrance: $Pe_{max}$=13.1. $Pe_{max}$ for the "Low" and "Mid" fragrances is less than $Pe_{min}$, so it is not possible to achieve both the maximum output rate for these fragrances and the response time. Nonetheless it is possible to achieve fractionation with all three fragrances.

Figure 23:
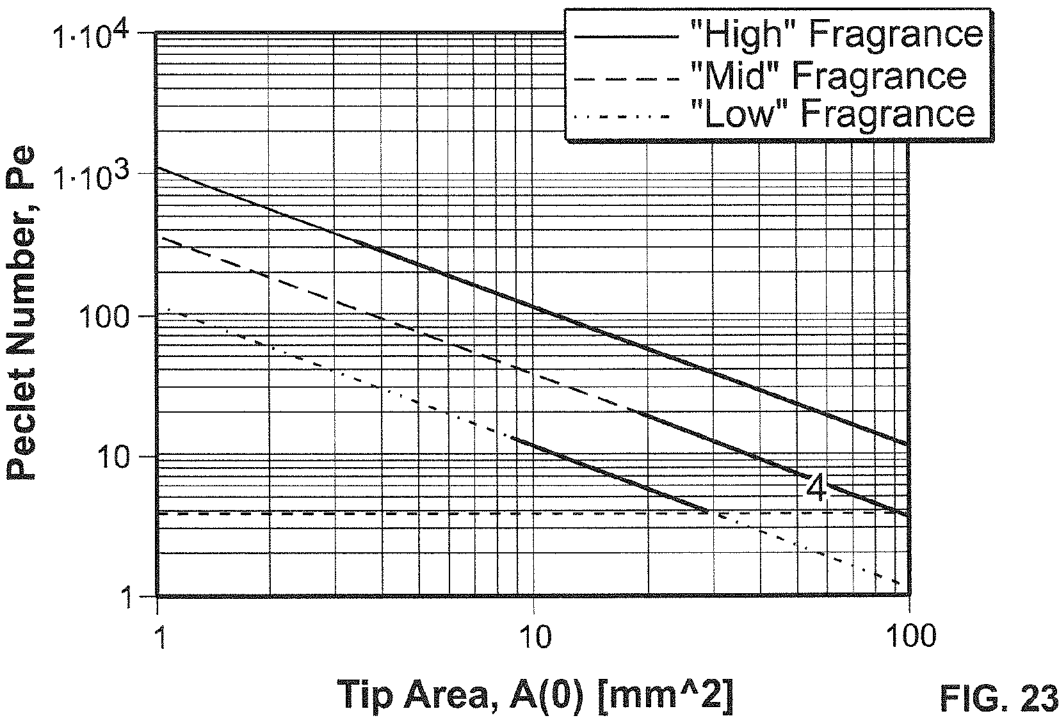
FIG. 23 is a graph depicting tip area versus Peclet number for a tapered wick with free convection.

FIG. 23 shows FIG. 14 applied to a free convention system employing a tapered wick and using only the fractionation requirement for $Pe_{min}$. A tip area, A(0) between 20 $mm^2$ and 30 $mm^2$ satisfies the constraints for all three fragrances, i.e. it falls within the thick line segments on their Pe~A(0) curves. Choosing the smallest area will give the smallest settling time, even though this will be longer than the required response time for the "Mid" and "Low" fragrances. Choosing A(0)=20 $mm^2$, the range of suitable pore sizes is given by Equation 25:

$$0.65\text{ um} = \frac{40\mu L a_{-1}}{\sigma A(0)} Q << d << \frac{2\sigma}{\rho g L} = 127\text{ um}$$

where the value on the left is largest for the "High" fragrance. Again there is a lot of freedom in the choice of pore size d.

Embodiment 3

Capillary Feeding a Sintered Wick

Figure 24:
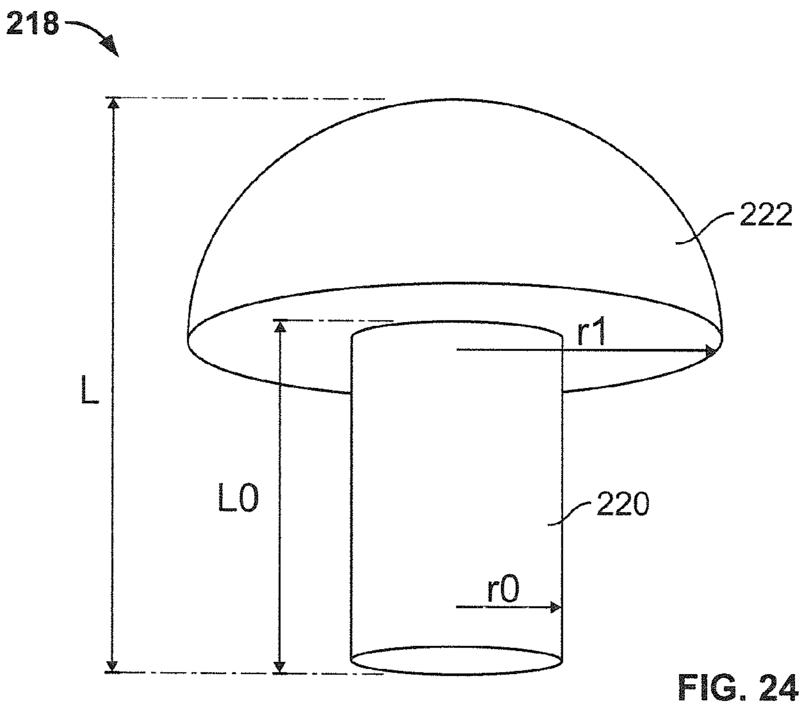
FIG. 24 is a bottom isometric view of a wick having a capillary feeding a sintered hemispherical wick.

FIG. 24 shows a design for wick 218 having a capillary 220 feeding a hemispherical sintered wick 222, wherein the capillary 220 has a radius r0 and a length L0 and the wick 222 has an outer radius r1. An overall length L of the wick 218 is L=L0+r1. The capillary 220 may be a single tube or a bundle of tubes. The capillary 220 has an inner diameter d0 and a porosity ϵ0 and the sintered wick 222 has a pore size d1 and a porosity ϵ1.

Using the wick 218, it will now be shown that it is easy to achieve very large values for the area factor $a_{-1}$, which results in very large Peclet numbers. In particular, the large surface area of the hemisphere of the sintered wick 222 creates a good output rate, which creates a large flow velocity through the capillary 220, easily overcoming diffusion within the capillary 220. In other words, fractionation is very easily established and only the response time places an upper bound on the tip area. The large Peclet numbers also simplify the design equations. This is fortunate, because otherwise the design methodology described above would become circular: the area factor $a_{-1}$ is chosen in Step 1, which requires setting r0, r1, and L0, but the tip area is calculated in Step 4, which dictates r1.

In the hemispherical sintered wick 222, the flow will pass through hemispherical shells of material with radii ranging from r0 to r1. The (free) area at radius r is:

$$A(r) = 2\pi\varepsilon 1 r^2 \text{ and the area factor is:} \quad \text{Equation 33}$$

$$a_{-1} = \frac{1}{L}\int_{-L}^{0}\frac{A(0)}{A(z)}dz \quad \text{Equation 34}$$

$$= \frac{1}{L}\left[\frac{2\pi\varepsilon 1 r1^2}{\pi\varepsilon 0 r0^2}L0 + \int_0^1 \frac{2\pi\varepsilon 1 r1^2}{2\pi\varepsilon 1 r^2}dr\right]$$

$$= \frac{2L0r1\varepsilon 1 + \varepsilon 0 r0 r1 - \varepsilon 0 r0^2}{(L0 + r1)\varepsilon 0}\frac{r1}{r0^2}$$

In the case that L0>>r0 (i.e. the capillary is long and thin), the area factor is well approximated by:

$$a_{-1} = 2\frac{\varepsilon 1}{\varepsilon 0}\frac{L0}{L0 + r1}\frac{r1^2}{r0^2} \quad \text{Equation 35}$$

The terms 2ϵ1/ϵ0 and L0/(L0+r1) are both roughly equal to about 1 and what makes potentially very large is the ratio $r1^2/r0^2$. This portion of Equation 35 could be made large by increasing r1, but this is limited by the overall length L=L0+r1, or by decreasing r0. The only limit to r0 is the need for surface tension to drive the flow through the capillary against viscous drag and gravity. This is expressed in Equation 25 in terms of a pore size d:

$$\frac{40\mu L a_{-1}}{\sigma A(0)} Q << d << \frac{2\sigma}{\rho g L}.$$

Using the expression for $a_{-1}$ in Equation 35 and A(0)=2πϵ1$r1^2$ allows the left hand side to be written in terms of r0:

$$\frac{40\mu L}{\pi\varepsilon 0\sigma r0^2} Q << d << \frac{2\sigma}{\rho g L} \quad \text{Equation 36}$$

In addition, in the capillary 220, the pore size cannot be bigger than 2r0, i.e.

$$d < 2r0. \text{ So, } \frac{40\mu L a_{-1}}{\sigma A(0)} Q << 2r0. \quad \text{Equation 37}$$

$$r0 >> \left[\frac{20}{\pi\varepsilon 0}\frac{\mu}{\sigma}L0Q\right]^{1/3}$$

Using L0=50 mm and Q=$Q_{max}$ for the "High" fragrance gives r0>>74 um. If we choose r0=300 um, r1=10 mm, L0=40 mm, and ϵ1=ϵ0, this gives $a_{-1}$=890, i.e. a very large number. As will be seen hereinbelow, the value of r1 actually needs to be chosen with all the fragrances in mind, but still results in a large value for $a_{-1}$.

A large value of $a_{-1}$ gives large values for the individual Peclet numbers, $$P_i = V_i\frac{a_{-1}L}{\delta}.$$

As discussed above, the average Peclet number Pe can then be closely approximated by the harmonic mean of the individual Peclet numbers $P_i$. Doubling the area factor $a_{-1}$ then just doubles both the $P_i$ and Pe. In this case, it is preferable for the design method to work with the tip Peclet number qe instead of the average Peclet numbers. The tip Peclet number qe is the harmonic mean of $q_i=P_i/a_{-1}=V_iL/\delta$:

$$qe = \left[\sum_i \frac{b_i}{q_i}\right]^{-1} = \frac{L}{\delta}\left[\sum_i \frac{b_i}{V_i(T)}\right]^{-1} \quad \text{Equation 38}$$

The lower limit on qe comes from the response time requirement (c.f. Equation 30):

$$q^e_{min} = L\sqrt{\frac{10}{Dt_r}} \quad \text{Equation 39}$$

For each fragrance, there is an upper limit on qe, $qe_{max}$, corresponding to using $\delta=\delta_{min}$ and/or $T=T_{max}$ in Equation 37. The tip area $A(0)$ can be chosen by considering the output rate Q to be a function of $A(0)$ and qe (c.f. Equation 31):

$$Q = qe\frac{DA(0)}{L} \quad \text{Equation 40}$$

A plot similar to that of FIG. 14 can be constructed to assist in the choice of $A(0)$ with the Pe axis replaced by the qe axis.

In a forced convection system, the minimum tip Peclet number is $qe_{min}=20.8$. Using Equation 37, the maximum tip Peclet numbers for the respective fragrances are: (1) "High" fragrance: $qe_{max}=402$; (2) "Mid" fragrance: $qe_{max}=21.5$; and (3) "Low" fragrance: $qe_{max}=15.1$. As is evident, $qe_{max}$ for the "Low" fragrance is less than $qe_{min}$, so it is not possible to achieve both the maximum output rate for that fragrance and the response time and, therefore, some compromise will be required.

Figure 25:
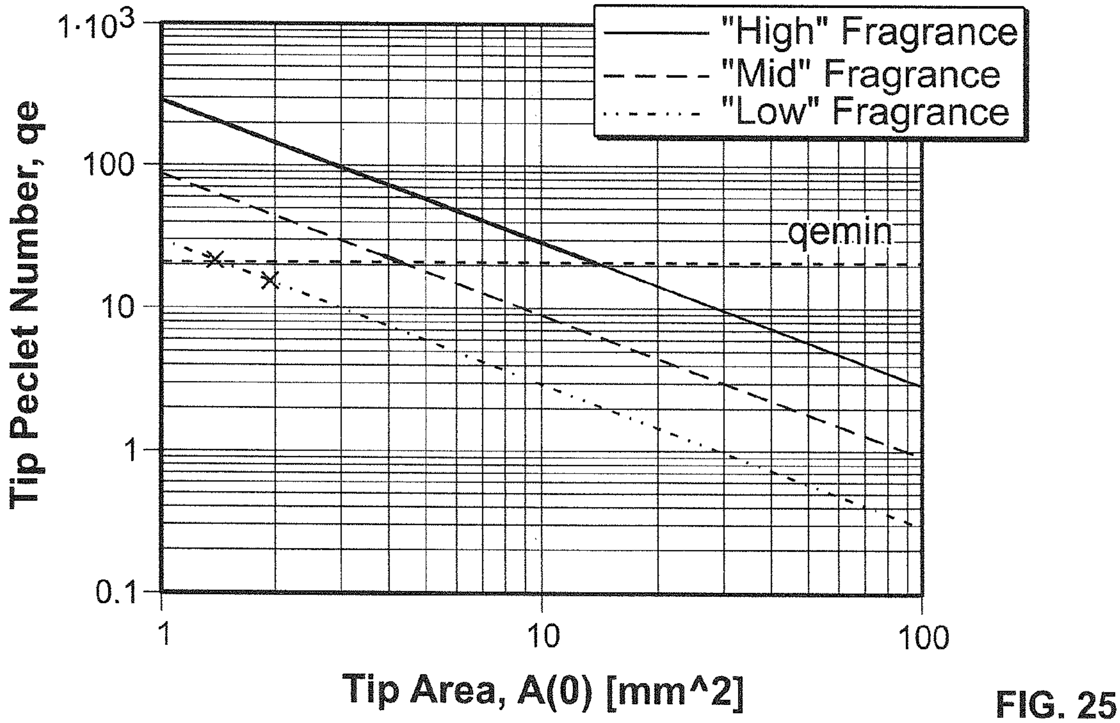
FIG. 25 is a graph depicting tip area versus Peclet number for the wick of FIG. 24 with forced convection.

FIG. 25 shows FIG. 14 applied to the forced convection system utilizing the capillary feeding the sintered wick (with a qe axis instead of a Pe axis). A tip area of $A(0)=4$ mm$^2$ satisfies the constraints for both the "High" and "Mid" fragrances, i.e. it falls within the thick line segments on their qe~A(0) curves. For the "Low" fragrance, this choice of $A(0)$ means that the maximum output rate will be achieved at a tip Peclet number less than $qe_{min}$, which means the settling time will be longer than the desired response time. Choosing A(0)=4 mm$^2$, the range of suitable pore sizes is given by Equation 25:

$$0.8 \text{ um} = \frac{40\mu La_{-1}}{\sigma A(0)}Q << d << \frac{2\sigma}{\rho pL} = 127 \text{ um}$$

where the value on the left is largest for the "High" fragrance. Again, there is a lot of freedom in the choice of pore size d.

In a free convention system, we will assume that the same 8-T characteristic as shown in FIG. 20 and as used for the straight wick applies. Again, the largest achievable tip Peclet number occurs at $T=T_{max}$ and $\delta=0.46$ mm. Using Equation 37, the maximum tip Peclet numbers for the respective fragrances are: (1) "High" fragrance: $qe_{max}=87.6$; (2) "Mid" fragrance: $qe_{max}=4.69$; and (3) "Low" fragrance: $qe_{max}=3.28$. As can be seen, $qe_{max}$ for the "Low" and "Mid" fragrances is less than $qe_{min}$, so it is not possible to achieve both the maximum output rate for these fragrances and the response time.

Figure 26:
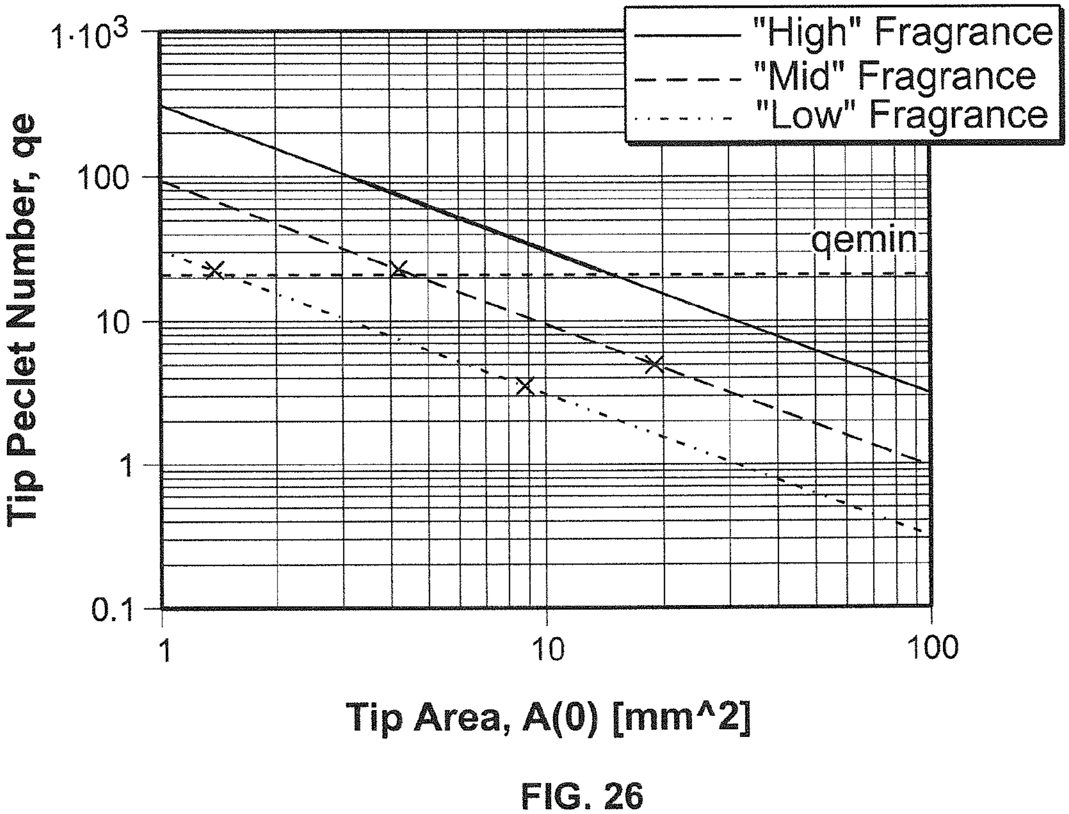
FIG. 26 is a graph depicting tip area versus Peclet number for the wick of FIG. 24 with free convection.

FIG. 26 shows FIG. 14 applied to the free convection system utilizing the capillary feeding the sintered wick (with a qe axis instead of a Pe axis). A tip area A(0) between 4.5 mm$^2$ and 15 mm$^2$ satisfies the constraints for the "High" fragrance, i.e. it falls within the thick line segments on its Pe~A(0) curve. Choosing the smallest area will give the smallest settling time, even though this will be longer than the required response time for the "Mid" and "Low" fragrances.

Embodiment 4

Parallel Wick Sections

A straight wick made of a bundle of capillary tubes has a theory of design identical to that of the sintered straight wick of the first embodiment. The only difference is that an output rate of the straight wick with a bundle of capillary tubes can be controlled in a different way, in particular, by blocking off a number of the tubes rather than varying a tip temperature and/or an air flow. This control method allows for reducing the output rate without reducing the Peclet number (which would result in poor fractionation) and without increasing the settling time.

Test Results

Experiment 1

Figure 27:
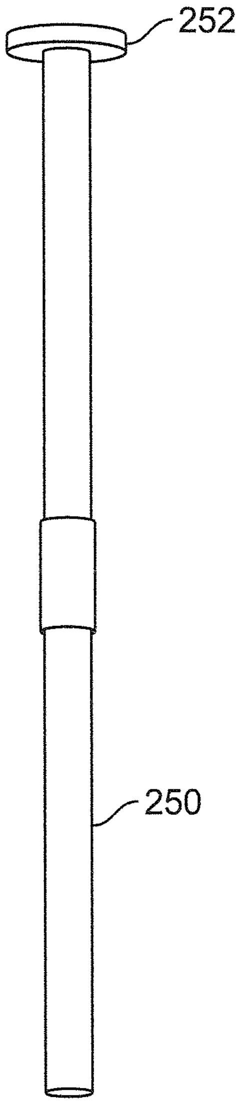
FIG. 27 depicts a wick having a generally cylindrical stem and a disc-shaped evaporation surface.
Figure 28:
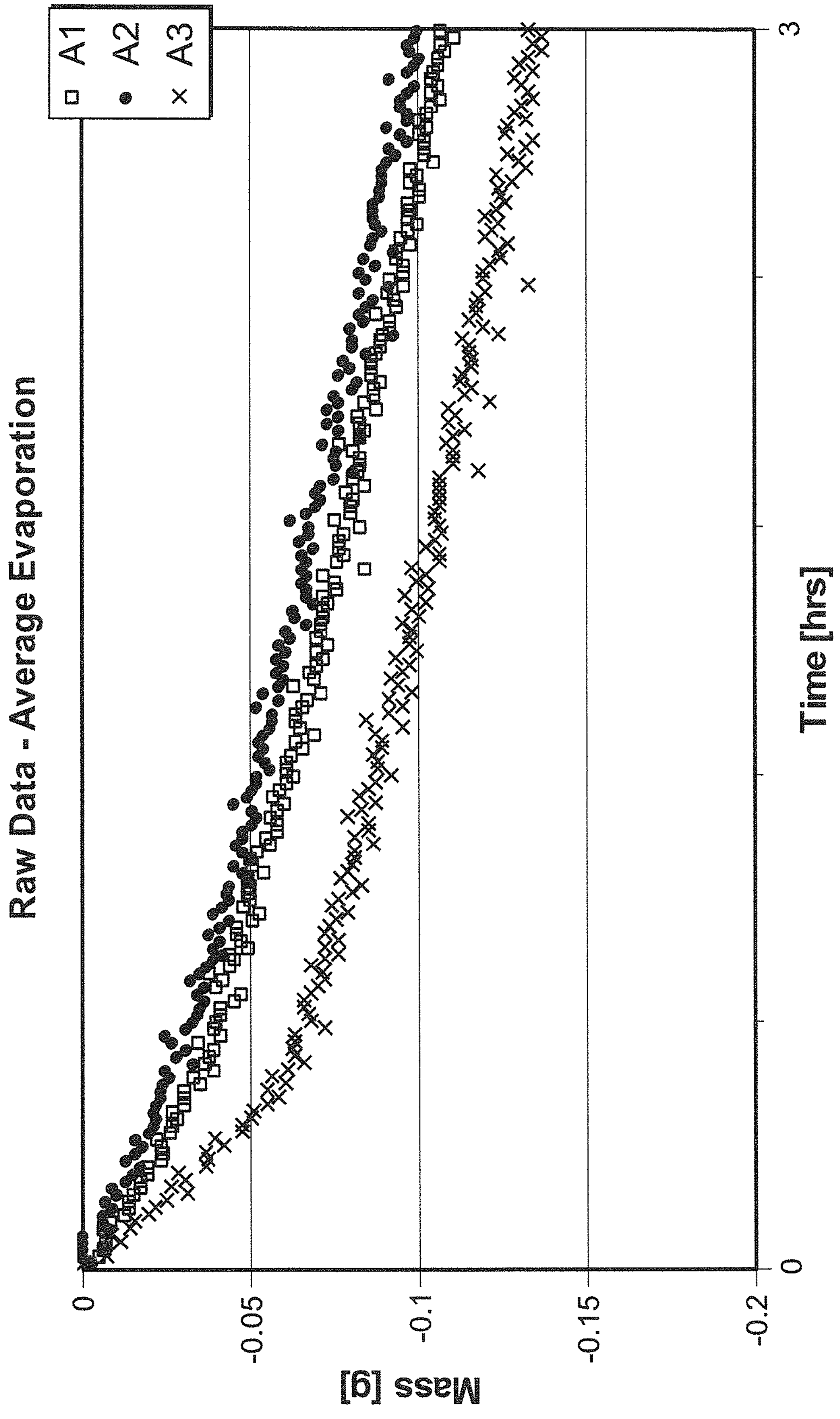
FIG. 28 is a graph depicting mass lost over a period of about 3 hours for three samples of the wick of FIG. 27.
Figure 29A:
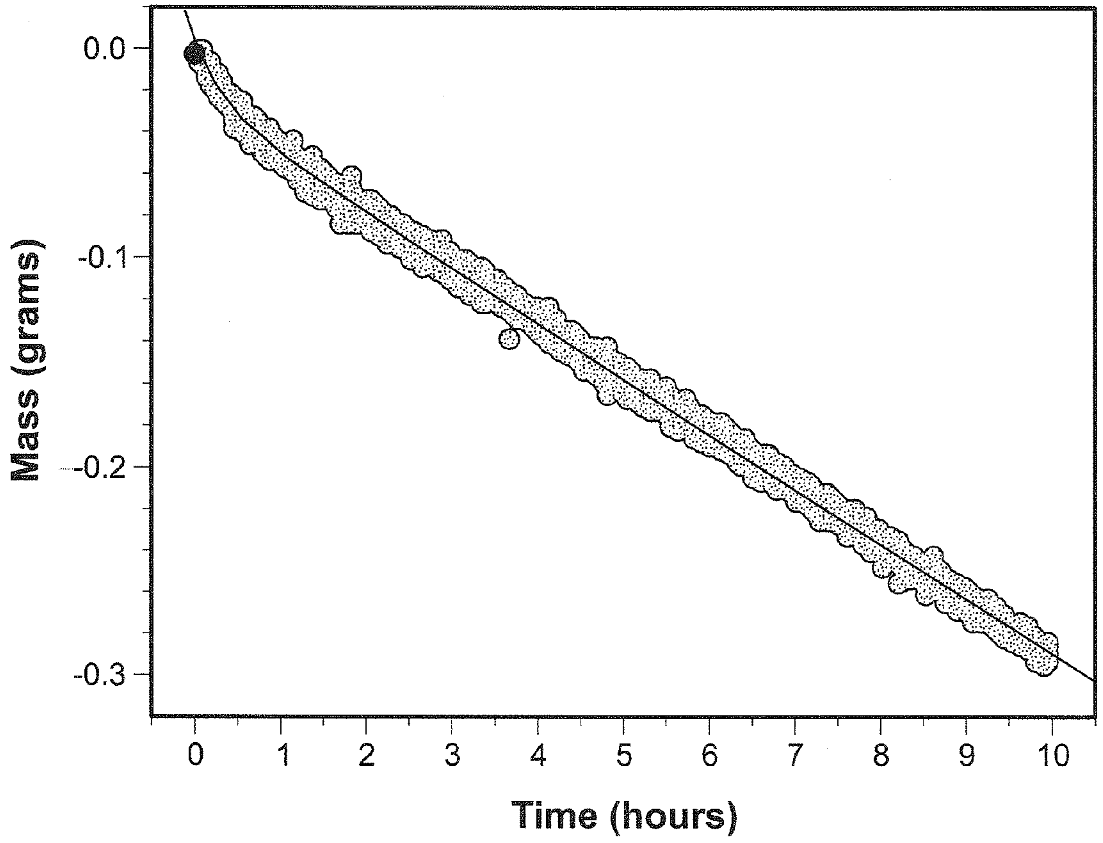
FIGS. 29A and 29B is a graph depicting mass lost over a period of about 10 hours for only two of the sample wicks charted in FIG. 28 and a best fit curve for such wicks, with FIG. 29B also showing various parameters used in calculating a predicted total mass lost at any given period of time.
Figure 29B:
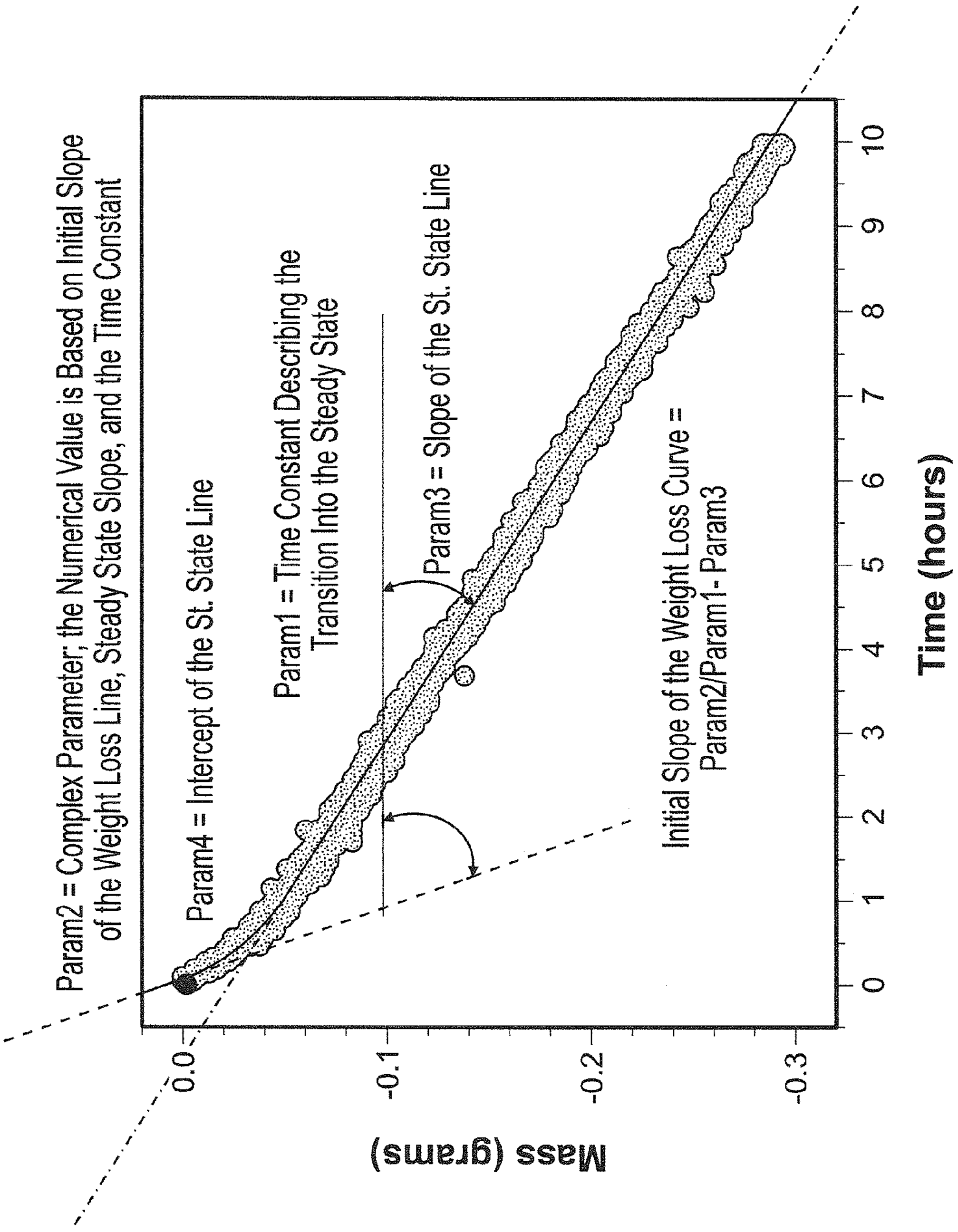

A first test was conducted using a first refill having a container and 15 grams of a liquid including a 1:1 molar mixture of decane (C10) and tetradecane (C14) normal alkanes disposed within the container. The container is the container utilized in the commercially available refill sold by S. C. Johnson & Son, Inc. and including a symmetrical body with front and rear walls having shell-shaped protrusions extending therefrom. A first sintered wick, as seen in FIG. 27, having a first generally cylindrical portion 250 with a diameter of about 0.105 inch (2.5 mm) and a disc-shaped evaporation surface 252 disposed at one end of the cylindrical portion 250 and having a diameter of about 0.25 inch (6.35 mm) and a thickness of about 0.14 inch (3.5 mm) was inserted within the container in contact with the fragrance to form the refill. Before insertion, a protective sheath was inserted over the stem to protect the stem during the application of heat. An evaporation surface area of the wick is therefore about 0.0491 in$^2$ (31.67 mm$^2$). Three refills were installed within standard plug-in scented oil devices, in particular, within the commercially available PlugIns® Scented Oil devices sold by S. C. Johnson & Son, Inc., with a section of the cylindrical portion 250 and the evaporation surface 252 of the wick disposed adjacent a heater of the device. Each device was set to a highest heat setting of "5," powered at 120 volts. The refills were placed on balances and the refills were weighed every minute for between two and three days. FIG. 28 depicts the mass (in grams) of the liquid lost versus time (in hours) for each of the refills (A1, A2, A3). The refill A3 was found to have behaved strangely, in particular, the liquid evaporated more quickly at the beginning of the test. This is a common occurrence and, for this reason, A3 was eliminated/rejected from the study. FIG. 29A depicts the mass (in grams) of the liquid lost versus time (in hours) for only the non-rejected refills A1, A2 over a period of 10 hours and FIG. 29B depicts the same graph as shown in FIG. 29A with explanations of the parameters of Equation 41, as set forth and described in detail below.

Figure 30:
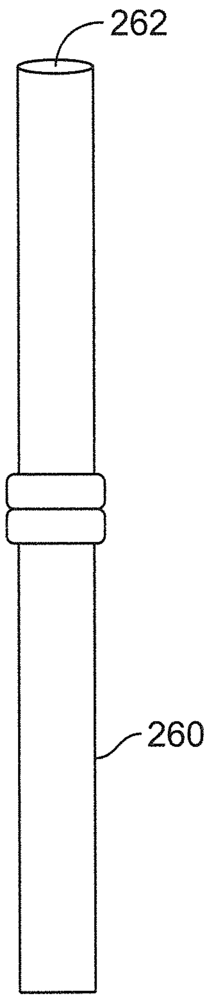
FIG. 30 depicts a wick having a generally cylindrical stem.
Figure 31:
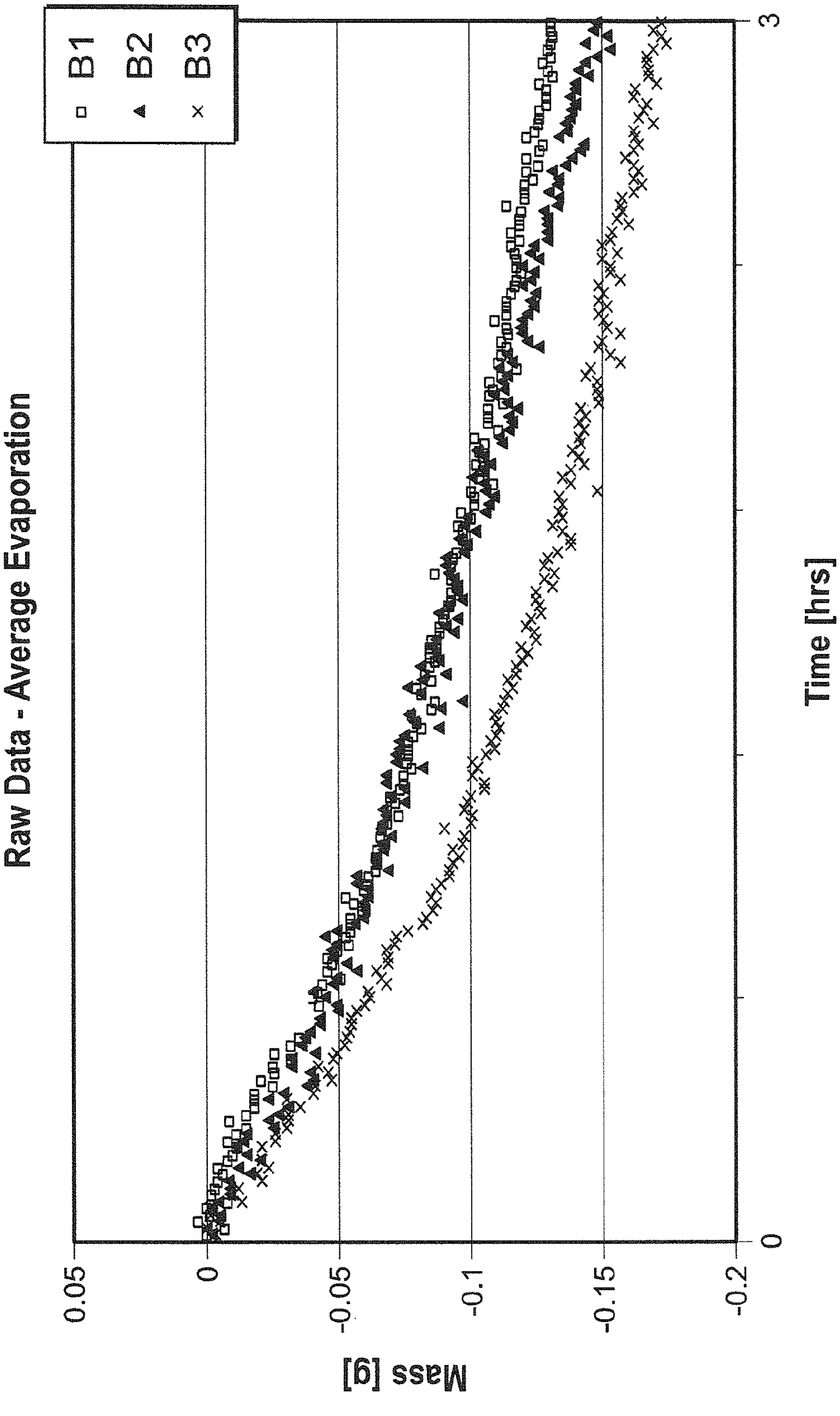
FIG. 31 is a graph depicting mass lost over a period of time of about 3 hours for three samples of the wick of FIG. 30.
Figure 32:
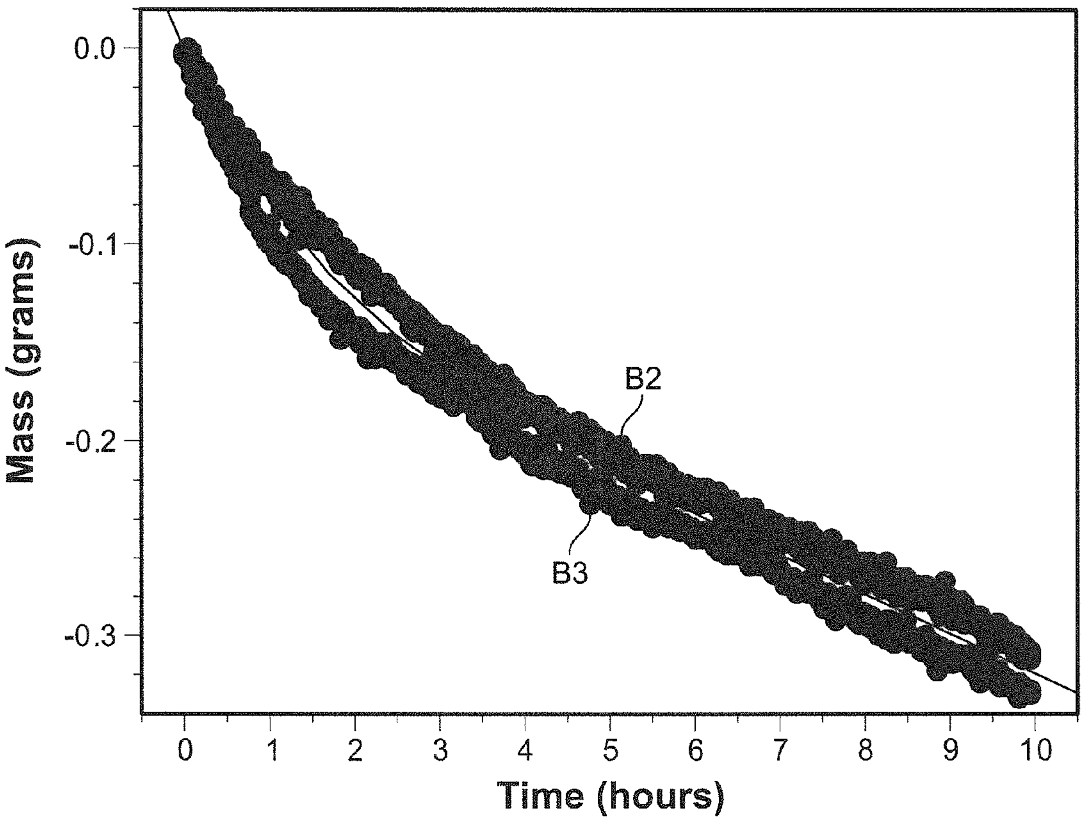
FIG. 32 is a graphs depicting mass lost over a period of about 10 hours for only two of the sample wicks charted in FIG. 31 and a best fit curve for such wicks.

The first test further included a second refill having a container and 15 grams of liquid including a 1:1 molar mixture of decane (C10) and tetradecane (C14) normal alkanes disposed within the container. The container is the container utilized in the commercially available refill sold by S. C. Johnson & Son, Inc. and including a symmetrical body with front and rear walls having shell-shaped protrusions extending therefrom. A second sintered wick, as seen in FIG. 30, having a generally cylindrical portion 260 with a diameter of about 0.25 inch (6.35 mm) was disposed within the container in contact with the fragrance. An evaporation surface area 262 of the wick is the same as the diameter of the wick and the same as the evaporation surface area of the wick disposed within the first refill, which is 0.0491 $in^2$ (31.67 $mm^2$). The refill was installed within a standard plug-in scented oil device, such as the PlugIns® Scented Oil device sold by S. C. Johnson & Son, Inc., with an upper section of the cylindrical portion 260 disposed adjacent a heater of the device. Each device was set to a highest heat setting of "5," powered at 120 volts. The refills were placed on balances and the refills were weighed every minute for between two and three days. FIG. 31 depicts the mass (in grams) of the fragrance lost versus time (in hours) for each of the refills (B1, B2, B3). The refill B1 was found to have behaved strangely in comparison to the refills B2 and B3, and thus, was rejected from the study. FIG. 32 depicts the mass (in grams) of the liquid lost versus time (in hours) for only the non-rejected refills B2, B3 over a period of 10 hours.

Equation 41 below was utilized to fit the data collected for the refills A1, A2 and B2, B3 to a non-linear model including 4 parameters, as follows:

$$\text{Predicted mass change}=\text{Parameter4}+(\text{Parameter3}*T)+(\text{Parameter2}*\exp(-T/\text{Parameter1})) \qquad \text{EQUATION 41}$$

where the predicted mass change is a predicted mass change at time T for each time point calculated by the best fit equation to determine the non-linear model (as seen by the solid lines in FIGS. 29A and 32). Referring to FIG. 29B, Parameter 1 is a time constant, which describes how quickly the weight loss will turn into a steady state weight loss. Parameter 2 is complex parameter based on an initial slope of the weight loss line, a steady state slope, and a time constant, as shown in FIG. 29B. Parameter 3 is the steady state evaporation rate, which is the slope of a steady state line and Parameter 4 is the point on a weight change versus time graph where the steady state line intersects the weight change axis. In addition, "T" refers to the elapsed time for a particular data point. "Steady state" is the average evaporation rate at the point where the system(s) reach steady state or a consistent weight loss rate.

Statistical treatment of the data allows for estimating the parameter values of Equation 41, as well as the confidence limits for these estimates at a 95% confidence level. All data from the non-rejected datasets were used in conjunction with a software program by the name of JMP®, verions 5 and 9 (www.jmp.com) to determine estimates for the time constant and steady state evaporation rate. The estimated time constant for the first wicks (A1 and A2) was found to be 0.36 hour+/−0.06 hour with a steady state evaporation rate of about 0.026 grams/hour. The estimated time constant for the second wicks B2 and B3 was found to be 1.5 hour+/−0.2 hour with a steady state evaporation rate of about 0.020 grams per hour. The conclusion taken from these results is that the second wicks (B2 and B3) have a significantly higher time constant, which translates into a longer time to steady state (settling time). Another conclusion taken from these results is that there is a clear dependence on the geometry of the wick, for example, a wick having a thinner diameter stem that increases the flow of volatile material therethrough, and has a larger diameter evaporation surface area has a lower time constant, which translates into a shorter time to steady state. As will be demonstrated below, the time constant and the time to steady state are dependent on a few factors, one of them being wick geometry, so a system as a whole (i.e., dispenser, diffusion element(s), volatile material, wick. etc.) must be optimized to have a lower time constant and a higher Peclet number, as described below.

Referring to Equation 41, the term that includes Parameter 2 changes non-linearly with time. In fact, this term approaches zero as time progresses. At (time=3*time constant), the value of the exponential portion of this term is 0.05; the term has dropped 95% from its initial value. Therefore, by (time=3*time constant), the system is at 95% steady state.

As has been noted above, it is desired to maintain a bottle composition that is the same as the initial bottle composition. One way to do this is to create a system that forces the system into steady state as early as possible. This experiment shows that the time constant, which can be seen as an experimental manifestation of the Peclet number for the system, and decreases as a Peclet number increases, will influence the time to steady state. As noted above, it is desirous to have a higher Peclet number, and thus, it follows that it is desirous to have a lower time constant. In particular, in one embodiment, a system has a time constant of less than or equal to about 1.0 hour and great than 0 hour. In other embodiments, the time constant is less than or equal to about 0.9 hour and greater than 0 hour. In still other embodiments, the time constant is less than or equal to about 0.8 hour and greater than 0 hour.

To determine the time constant for a particular system, one would record the weight loss of the refill every minute and use Equation 41 to estimate the time constant, as described herein. Creating such data for multiple identical refills in the identical system and averaging or otherwise combining the data would achieve a more accurate time constant, although this is not necessary.

Experiment 2

Figure 33:
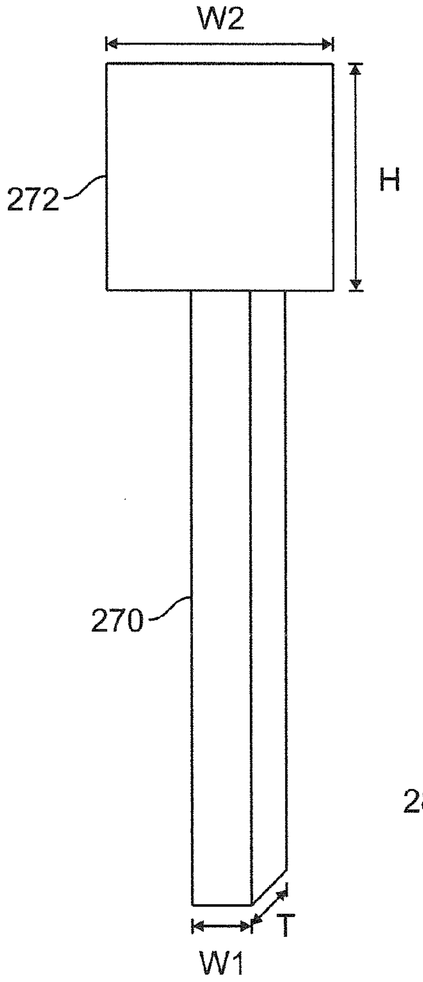
FIG. 33 is a diagrammatic depiction of a generally flat wick having an evaporation surface.
Figure 34:
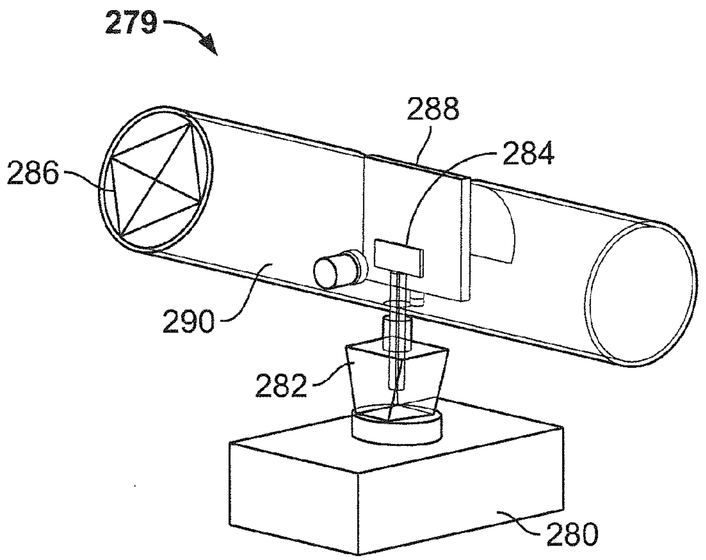
FIG. 34 is a system for evaporating a volatile material from the wick of FIG. 34.

In Experiment 2, a system and a refill with a wick were designed to analyze the effect of wick cross sectional area, wick pore size, wick surface area, and time on the evaporation rate profile, among other things. The wick, as seen in FIG. 33, was designed having a portion 270 in contact with the fragrance and an evaporation surface 272 extending out of the refill. The portion 270 has a width W1 and a thickness T and the evaporation surface 272 has a height H and a width W2. The width W1 is greater than the thickness T, and thus, the wick appears generally flat (even though the thickness T could vary along the width W1 and/or the width W1 could vary along the thickness T). The liquid utilized was the same as for Experiment 1. The system, as seen in FIG. 34, includes a volatile material dispenser (279). For testing purposes, the system includes a weighing scale 280 (accurate to 10 μm) on which the refill 282 having the wick 284 in contact with the liquid is received. The weighing scale 280 is utilized to make precise measurements as to how much of the liquid within the refill 282 has been dispensed (any change in weight in a precisely controlled system is due to weight loss of the liquid). The system includes a tunnel or other enclosed space with a fan 286 and a heater 288 disposed therein. The wick 284 extends into the tunnel such that the wick 284 is disposed adjacent the heater 288 and air from the fan 286 impinges upon the wick 284. An infrared probe 290 is also spaced from the evaporation surface 272 of the wick to measure an evaporation surface area thereof.

For Experiment 2, two sets of wicks were utilized with the first set of wicks having a thickness T of about 1.6 mm and the second set of wicks having a thickness T of about 4.8 mm, with all other dimensions of the wicks being the same between the two sets of wicks. The system of FIG. 34 was positioned in a room at room temperature and the fan was actuated. For each set of wicks, three different scenarios were tested, a first having a velocity of about 1 m/s through the tunnel, a second having a velocity of about 2 m/s through the tunnel, and a third having a velocity of about 3 m/s through the tunnel The heater was not activated. The data collected is shown in the chart below:

| Velocity | C (Wick with 1.6 mm thickness) TIME CONSTANT | C EVAPORATION RATE | D (Wick with 4.8 mm thickness) TIME CONSTANT | D EVAPORATION RATE |
|---|---|---|---|---|
| 1 m/s | 1.71 hour ± 0.04 hour | 0.007 grams/hour | 1.78 hour ± 0.011 hour | 0.011 grams/hour |
| 2 m/s | 1.15 hour ± 0.03 hour | 0.010 grams/hour | 1.16 hour ± 0.017 hour | 0.017 grams/hour |
| 3 m/s | 1.03 hour ± 0.05 hour | 0.014 grams/hour | 0.97 hour ± 0.07 hour | 0.022 grams/hour |

As expected, the steady state evaporation rates for wicks C and D increase as air flow increases (and presumably as temperature increases). In addition, for higher evaporations rates, a stem with a smaller cross-sectional area leads to shorter time constants, which is the desired result.

Figure 35:
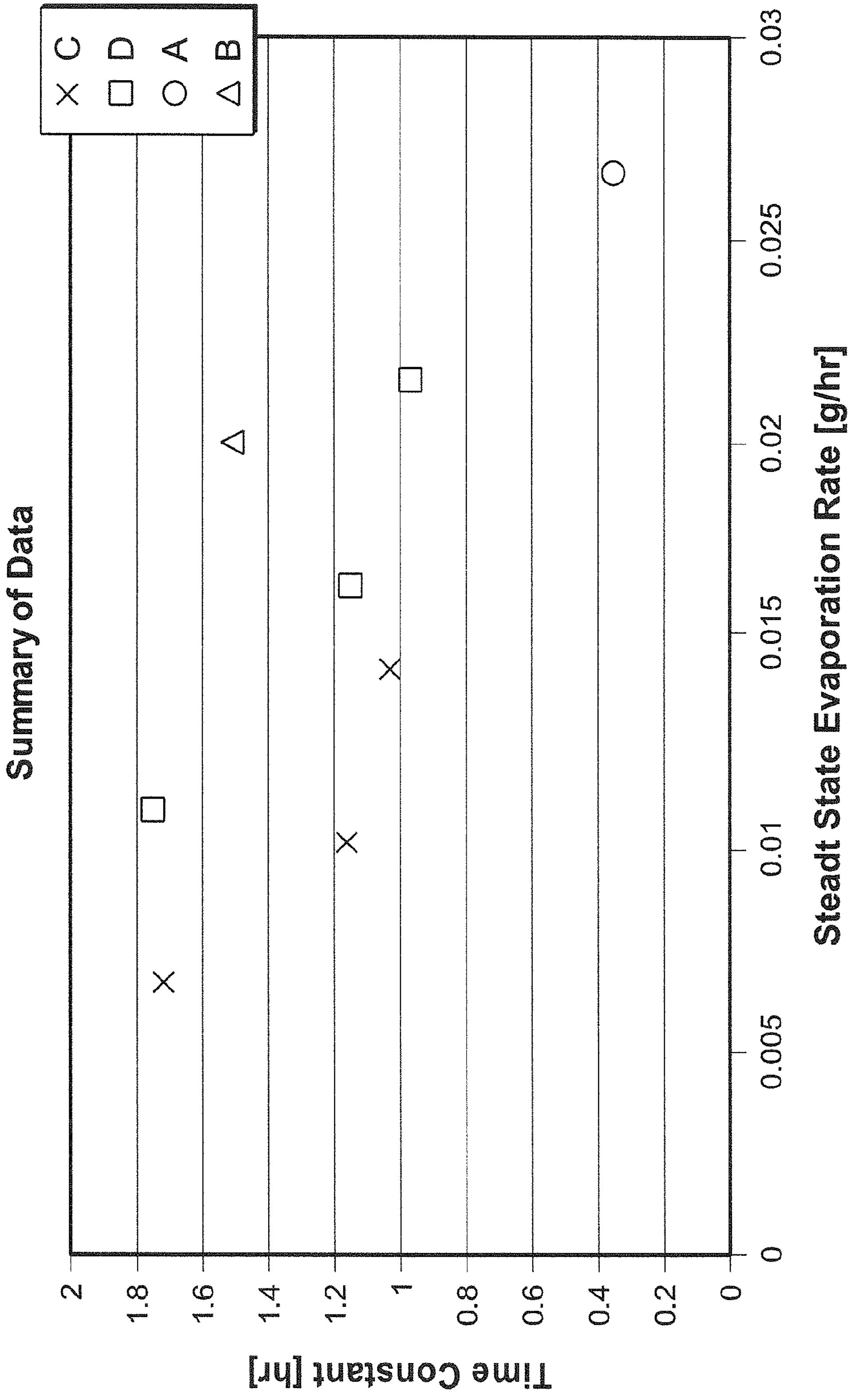
FIG. 35 is a graph depicting a time constant versus a steady state evaporation rate for the wicks of FIGS. 27, 30, and 33.

FIG. 35 plots the average time constants (hour) and steady state evaporation rates (grams/hour) for wicks A and B and also plots the time constants and evaporations rates for wicks C and D at each of the velocities of 1 m/s, 2 m/s, and 3 m/s (as shown in the chart above).

In summary, the second portion of Experiment 2 demonstrates that time (at least at the beginning) and an evaporation surface area have a strong effect on evaporation rate and pore size (of the wick) and the stem cross-sectional area have a weak effect on the evaporation rate. Using these findings, a wick and an evaporation surface can be selected that minimize the time to steady state, thereby minimizing the time during which the composition of the fragrance in the refill can change.

INDUSTRIAL APPLICABILITY

The systems and refills/wicks of the present disclosure are intended to allow for the emission of volatile material through a life of the refill that is generally the same as the initial refill composition before the refill has been installed within the system. Various parameters and equations are utilized to determine suitable systems and refills/wicks.

Numerous modifications to the present disclosure will be apparent to those skilled in the art in view of the foregoing description. Accordingly, this description is to be construed as illustrative only and is presented for the purpose of enabling those skilled in the art to make and use the disclosure and to teach the best mode of carrying out same. The exclusive right to all modifications within the scope of the impending claims is expressly reserved. All patents, patent publications and applications, and other references cited herein are incorporated by reference herein in their entirety.

We claim:

1. A system for consistently emitting a volatile material, the system including:

- a volatile material dispenser having a diffusion element; and
- a refill adapted for disposal within the volatile material dispenser and including a container having a volatile material disposed therein and a wick having a first end disposed in contact with the volatile material in the container and a second end extending out of the container;
- wherein a time that it takes a weight loss of the system to reach a steady state weight loss is less than or equal to about 1.0 hour.

2. The system of claim 1, wherein the time it takes the weight loss of the system to turn into steady state is less than or equal to about 0.9 hour.

3. The system of claim 2, wherein the time it takes the weight loss of the system to turn into steady state is less than or equal to about 0.8 hour.

4. The system of claim 1, wherein the wick includes a generally cylindrical stem having a first diameter and a generally disc-shaped evaporation surface disposed at the second end of the wick and having a second diameter that is greater than the first diameter.

5. The system of claim 4, wherein the second diameter is at least twice the first diameter.

6. The system of claim 1, wherein the wick is tapered outwardly between the first end and the second end.

7. The system of claim 1, wherein the wick includes a stem having a length, a width, and a thickness, wherein the thickness is less than the width and an evaporation surface disposed at the second end of the wick and having a width that is greater than the width of the stem.

8. The system of claim 1, wherein the wick includes a capillary tube with the first end disposed in contact with the volatile material and the second end extending out of the container and a hemispherical wick disposed adjacent the second end of the tube.

9. The system of claim 1, wherein the wick includes a plurality of capillary tubes that can be controlled by blocking off or opening up one or more tubes to change an output rate thereof.

10. The system of claim 1, wherein the diffusion element is a heater disposed adjacent the second end of the wick when the refill is inserted into the dispenser to aid in evaporating the volatile material from an evaporation surface of the wick.

11. The system of claim 10, wherein a composition of the volatile material generally remains the same throughout a life of the refill and remains generally the same as an initial refill composition before the refill has been installed within the dispenser.

12. The system of claim 1, wherein the diffusion element is a fan disposed within the dispenser and the wick of the refill is disposed within an air flow path created by the fan when the refill is installed in the dispenser to aid in evaporating volatile material from an evaporation surface of the wick.

13. The system of claim 12, wherein a composition of the volatile material generally remains the same throughout a life of the refill and remains generally the same as an initial refill composition before the refill has been installed within the dispenser.

14. The system of claim 1, wherein the wick includes a capillary tube with a first end disposed in contact with the volatile material and a second end extending out of the container and a hemispherical wick disposed adjacent the second end of the tube.

15. A system for consistently emitting a volatile material, the system including:

a volatile material dispenser having a diffusion element; and a refill adapted for disposal within the volatile material dispenser and including a container having a volatile material disposed therein and a wick having a first end disposed in contact with the volatile material in the container and a second end extending out of the container;

wherein the system reaches steady state in less than or equal to about 1.0 hour such that a composition of the volatile material when emitted remains substantially the same throughout a life of the refill and remains substantially the same as an initial refill composition before the refill has been installed within a dispenser.

16. The system of claim 15, wherein the system reaches steady state in less than or equal to about 0.8 hour.

17. The system of claim 15, wherein the wick includes a generally cylindrical stem having a first diameter and a generally disc-shaped evaporation surface disposed at the second end of the wick and having a second diameter that is greater than the first diameter and wherein the second diameter is at least twice the first diameter.

18. The system of claim 12, wherein the diffusion element is a heater disposed adjacent the second end of the wick when the refill is inserted into the dispenser to aid in evaporating the volatile material from an evaporation surface of the wick.

19. The system of claim 15, wherein the wick is tapered outwardly between the first end and the second end.

20. The system of claim 15, wherein the wick includes a plurality of capillary tubes that can be controlled by blocking off or opening up one or more tubes to change an output rate thereof.

* * * * *